United States Patent
Dick et al.

(10) Patent No.: US 10,094,817 B2
(45) Date of Patent: Oct. 9, 2018

(54) PROCESS AND PRODUCTION DEVICE FOR THE PRODUCTION OF AT LEAST ONE ANALYTICAL DEVICE

(71) Applicant: Roche Diagnostics Operations, Inc., Indianapolis, IN (US)

(72) Inventors: Siegfried Dick, Mannheim (DE); Markus Fischer, Moerlenbach (DE)

(73) Assignee: Roche Diagnostics Operations, Inc.

(*) Notice: Subject to any disclaimer, the term of this patent is extended or adjusted under 35 U.S.C. 154(b) by 195 days.

(21) Appl. No.: 14/611,611

(22) Filed: Feb. 2, 2015

(65) Prior Publication Data
US 2015/0233889 A1 Aug. 20, 2015

(30) Foreign Application Priority Data
Feb. 14, 2014 (EP) .................................... 14155139

(51) Int. Cl.
B05D 3/00 (2006.01)
B05D 7/00 (2006.01)
G01N 33/487 (2006.01)
B01L 3/00 (2006.01)
B32B 38/04 (2006.01)
(Continued)

(52) U.S. Cl.
CPC .......... *G01N 33/487* (2013.01); *B01L 3/5023* (2013.01); *B01L 3/502707* (2013.01); *B05D 3/007* (2013.01); *B05D 7/50* (2013.01); *G01N 33/4875* (2013.01); *B01L 2200/12* (2013.01); *B01L 2300/0645* (2013.01); *B01L 2300/0825* (2013.01); *B01L 2300/0887* (2013.01); *B01L 2400/0406* (2013.01); *B32B 37/12* (2013.01); *B32B 2038/045* (2013.01); *B32B 2041/04* (2013.01)

(58) Field of Classification Search
CPC ... G01N 333/487; B01L 3/5023; B05D 3/007; B05D 7/50
See application file for complete search history.

(56) References Cited

U.S. PATENT DOCUMENTS 3,961,346 A   6/1976   White
4,447,140 A   5/1984   Campbell et al.
5,067,309 A  11/1991   Carlberg et al.
(Continued)

FOREIGN PATENT DOCUMENTS

EP   1482299 B1   12/2004
EP   2055472 A1    5/2009
(Continued)

Primary Examiner — Dah-Wei D. Yuan
Assistant Examiner — Kristen A Dagenais-Englehart
(74) Attorney, Agent, or Firm — Roche Diagnostics Operations, Inc.

(57) ABSTRACT

A process for the production of at least one analytical device is disclosed. The analytical device comprises at least one capillary element. The process comprises providing at least one carrier layer; providing at least one spacer layer; applying the spacer layer on top of the carrier layer; providing at least one cover layer; and applying the cover layer on top of the spacer layer. The process further comprises at least one cutting step. At least one capillary channel of the capillary element is cut out from the spacer layer. The cutting step is performed by using at least two cutting tools. The cutting tools complement one another to form a contour of the capillary channel.

13 Claims, 9 Drawing Sheets

(51) Int. Cl.
   *B32B 37/12*     (2006.01)
   *B32B 41/00*     (2006.01)

(56) References Cited

U.S. PATENT DOCUMENTS

| | | | |
|---|---|---|---|
| 6,207,000 B1 * | 3/2001 | Schwobel | B01L 3/5023 |
| | | | 156/248 |
| 6,800,488 B2 | 10/2004 | Khan et al. | |
| 6,939,450 B2 | 9/2005 | Karinka et al. | |
| 7,086,277 B2 | 8/2006 | Tess et al. | |
| 2005/0000842 A1 * | 1/2005 | Timmerman | B26D 5/32 |
| | | | 206/449 |
| 2007/0278097 A1 * | 12/2007 | Bhullar | B01L 3/502715 |
| | | | 204/403.01 |
| 2012/0298294 A1 | 11/2012 | Manes et al. | |

FOREIGN PATENT DOCUMENTS

| | | |
|---|---|---|
| JP | S63-196850 A | 8/1988 |
| JP | 2007-216343 A | 8/2007 |
| WO | 2004/040287 A1 | 5/2004 |
| WO | 2009/056299 A1 | 5/2009 |
| WO | 2010/122059 A1 | 10/2010 |

* cited by examiner

PROCESS AND PRODUCTION DEVICE FOR THE PRODUCTION OF AT LEAST ONE ANALYTICAL DEVICE

CROSS-REFERENCE TO RELATED APPLICATIONS

This application claims priority to EP 14155139.0, filed Feb. 14, 2014, which is hereby incorporated by reference.

BACKGROUND

The present disclosure generally relates to a process and a production device for producing at least one analytical device and to an analytical device producible by the process, and in particular, to the field of manufacturing analytical devices such as test elements for detecting at least one analyte in a sample, such as for manufacturing test elements for detecting at least one analyte in a sample of a body fluid.

One or more analytes present in a body fluid may be detected, such as one or more analytes which may participate in a metabolism of a human or animal, such as, one or more analytes such as glucose, lactate, triglycerides or cholesterols. The body fluid may be an arbitrary body fluid, such as blood, interstitial fluid, ocular fluid, tear fluid, saliva or urine. Other embodiments are feasible. The analytical device specifically may be applicable in the field of professional monitoring or in the field of home monitoring of at least one health state of a person, such as in the field of diabetes care. Other uses are feasible.

In the field of medical technology, specifically in the field of medical analytics, a large number of analytical devices are known. In the following, without wishing to restrict the present disclosure to specific embodiments, the present disclosure is explained in view of the production of test elements for detecting at least one analyte in a sample, such as in a sample of a body fluid. However, other types of analytical devices having at least one capillary element are feasible.

Analytical devices, such as test elements, often are produced by using continuous processes, using cutting techniques, wherein the analytical devices are cut from one or more continuous webs or tapes. Cutting processes are well known in the art such as, as an example, an apparatus for cutting and assembling batches of diagnostic strips and for transferring predetermined numbers of strips into bottles or the like. The apparatus has a rotary knife set which slits cards into strips and directs alternate ones of the strips into slots on one side of a carrier and directs the others of the strips into slots at the opposite side of the carrier. The strips are delivered to collection chambers for transfer to vials, by relative movement of the carrier and collection chambers.

One major technical challenge in the production of analytical devices, such as in the production of test strips, is the mass-production of fluidic structures. Thus, as an example, many analytical devices comprise one or more capillary elements, for example for transporting a sample of a fluid from an application position to an analysis position within the analytical device. For providing capillary elements in a continuous process, a process for the production of analytical devices is known. The analytical devices include analytical test elements with a capillary-active zone for examining fluid samples. In the process, a carrier layer is prepared, a spacer layer is laminated onto the carrier layer, a contour is punched, cut or stamped through the spacer layer laminated onto the carrier layer which determines the shape of the capillary-active zone. Those parts of the spacer layer which are not required to form the capillary-active zone are removed from the carrier layer, and a cover layer is applied to the spacer layer to result in a capillary-active zone.

Despite the advantages, a large number of technical challenges remain. Thus, the process is limited with regard to the width of the capillary elements. Thus, specifically, thin capillary elements, having a width of below 2 mm, remain a challenge, depending on the strength or thickness of the spacer layer. Thus, often, double-sided adhesive tapes are used. With increasing thickness of the adhesive tapes, however, the minimum width of the capillary element producible by the cutting process increases. This is due to the fact that a rotary cutting tool having at least two opposing blades is used, in order to cut out those parts of the spacer layer which are not required for shaping the capillary-active zone, i.e. the inner part of the capillary elements. This cutting tool, however, in most cases fails to provide sufficient space for pushing aside the unwanted inner part of the capillary element. As a result, specifically when cutting the capillary element on the carrier layer, the capillary activity may be reduced, and residuals of an adhesive within the capillary channel may remain. Further, the cutting tool may even be damaged or destroyed during the cutting process, since the cutting blades or edges in many cases are unable to stand the pressure of the material pushed aside during the cutting process.

A further technical challenge involved in known processes for continuous manufacturing of analytical devices resides in the accuracy of positioning. Thus, specifically when manufacturing a capillary element for application onto a pre-manufactured carrier having one or more structures such as having one or more electrodes already manufactured by printing or laser ablation techniques, rotary cutting tools and endless cutting processes often fail to provide the possibility of compensating for positioning errors. Since the rotary cutting tools provide a fixed surface ratio, the system often is not capable to compensate for continuous changes. Thus, known devices and processes often are unable to compensate for abrupt or continuous changes of process parameters. Consequently, known processes lead to a reduced yield which, mainly, is due to the endless rotary cutting tool which is in continuous engagement with the layer to be cut.

A further disadvantage resides in the fact that the divisor, i.e. the ratio of the capillary width and the distance between neighboring capillaries, remains constant in the process. Consequently, in case the rotary cutting tool is controlled, the width and the position of both the capillary and the non-capillary part of the analytical device are changed simultaneously, thereby keeping the ratio of these two dimensions unchanged. Consequently, manufacturing a capillary element having a constant capillary width, with a varying divisor, is not feasible by known processes.

Therefore, this is a need for a process and a production device for the production of at least one analytical device such as at least one test element that is suited for mass-manufacturing in a continuous process of test elements such as test strips that have one or more capillary elements manufactured with a low width of the capillary elements, such as a width of less than 2 mm or even less than 1.5 mm with a variable divisor and a high-precision control of the width of the capillary elements and the divisor.

SUMMARY

According to the present disclosure, a process for the production of at least one analytical device is disclosed. The analytical device can have at least one capillary element. The process can comprise providing at least one carrier layer and at least one spacer layer. The spacer layer can be applied on top of the carrier layer. At least one cover layer can be provided. The cover layer can be applied on top of the spacer layer. At least one capillary channel of the capillary element can be cut out from the spacer layer. The cutting out is performed by using at least two cutting tools. The cutting tools can complement one another to form a contour of the capillary channel.

Accordingly, it is a feature of the embodiments of the present disclosure to provide a process and a production device for the production of at least one analytical device such as at least one test element that is suited for mass-manufacturing in a continuous process of test elements such as test strips that have one or more capillary elements manufactured with a low width of the capillary elements, such as a width of less than 2 mm or even less than 1.5 mm with a variable divisor and a high-precision control of the width of the capillary elements and the divisor. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
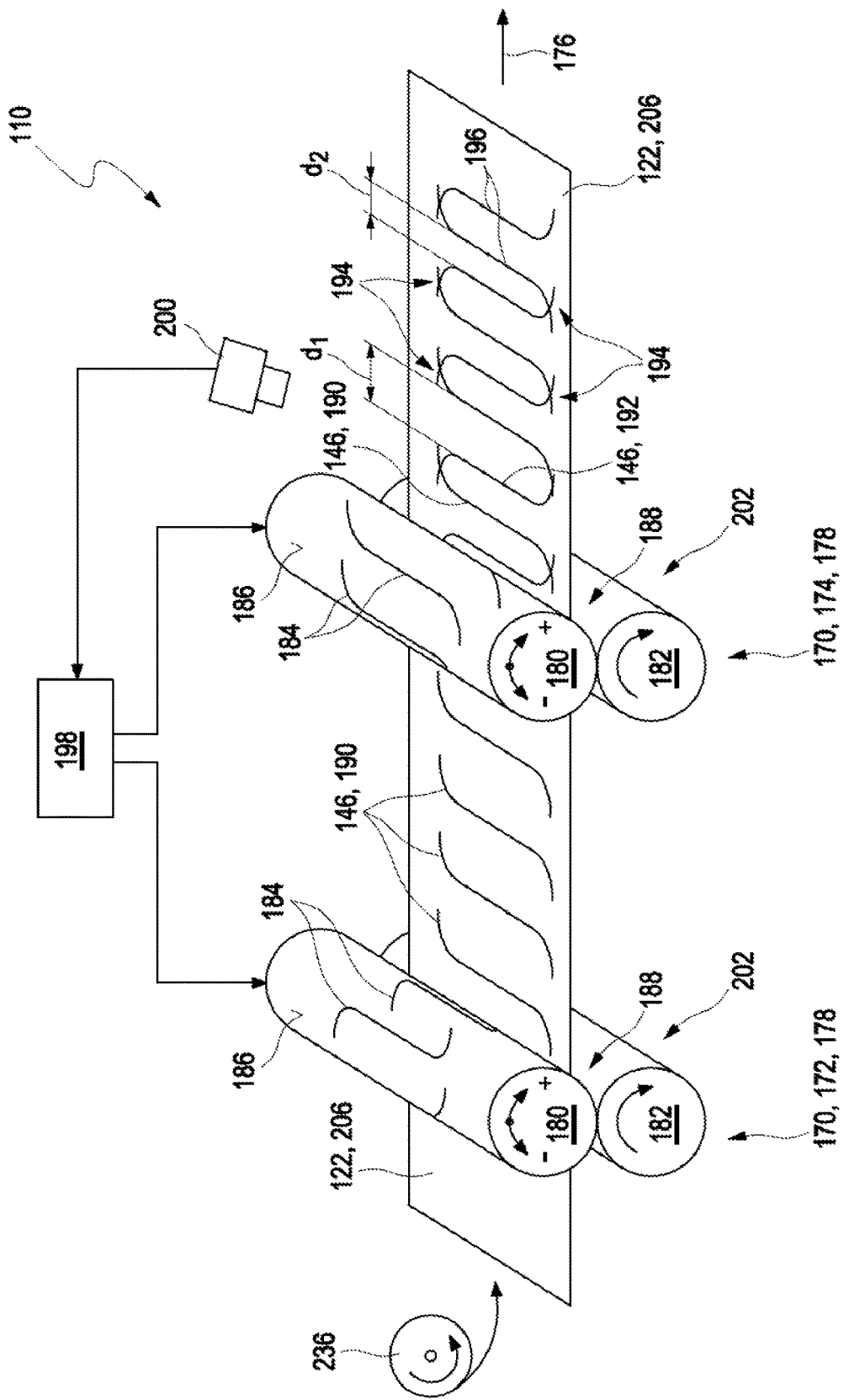
FIG. 1 illustrates a cutting tool for a production device for the continuous production of analytical devices according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A process for the production of at least one analytical device is disclosed. Specifically, the process may be a continuous process which, at a constant or variable rate, sequentially and/or in parallel, can provide a large number of analytical devices, such as at least 10, at least 100, at least 1000 or at least 10000 analytical devices. Thus, as will be outlined in further detail below, the process may be embodied as a continuous process in the form of a web process or a tape process, such as a reel-to-reel process or a reel process. Thus, the raw materials which may be used for the process may be provided by one, two, three or more reels, in the form of continuous tapes or webs, leading to an intermediate product in the form of a multi-layer tape and/or web, which, subsequently, may be cut into the analytical devices.

As used herein and as partly explained above, an analytical device generally may be an arbitrary analytical device which may serve one or more analytical purposes. Thus, the analytical device may be or may comprise a test element, i.e. an element adapted for determining one or more physical, chemical or biological properties or parameters of a sample. As an example, the analytical device may be or may comprise a test element for analyzing a sample of a body fluid, such as one or more of the body fluids listed above. Thus, for example, the analytical device may be a test element for detecting one or more analytes in a sample and/or for measuring one or more parameters of the sample, such as in a sample of a body fluid, such as one or more of the analytes listed above. In the following, without wishing to exclude further embodiments, the present disclosure will be explained in the context of manufacturing test elements for detecting one or more of glucose, triglycerides, lactate or cholesterols in blood or other body fluids. Additionally or alternatively, test elements may be manufactured which are capable of detecting and/or measuring one or more parameters such as coagulation parameters, such as prothrombin time, a PTT, ACT or any arbitrary combination thereof. As an example, the test element may be a test strip, i.e. a test element having the shape of a strip, such as a rectangular strip. As used herein, the term strip generally refers to a flexible and/or deformable, flat element, the lateral extension of which exceeds its thickness by far, such as by at least a factor of 5, more preferably by at least a factor of 10 or by at least a factor of 100.

The analytical device can have at least one capillary element. As used herein, a capillary element can generally refer to a microfluidic element which, by capillary forces, can be capable of transporting fluids, such as aqueous fluids. Thus, the capillary element may provide one or more channels which can be suited to exert a capillary force onto a fluid. The capillary element, such as the capillary channel, may be a closed capillary channel, which, in a direction perpendicular to an axis of extension of the capillary channel, can be surrounded by capillary walls. Additionally, however, parts of the capillary channel may be opened, such as by providing parts of the capillary channel as an opened capillary slit. The capillary channel may be straight or may be bent. Further, more complex capillary elements may be provided, such as capillary elements having one, two, three or more capillary channels. As an example, the capillary element may simply comprise a straight capillary channel, such as a capillary channel leading from an application position for applying a sample of a fluid to the capillary channel to one or more analytical positions, in which one or more properties of the fluid may be determined. Thus, the application position may be close to an edge of the analytical device, such as on a front face of a test strip and/or on a surface of the test strip close to an edge of the test strip. The capillary element, such as the capillary channel, may be oriented essentially parallel to a longitudinal axis and/or an axis of extension of the test element, such as parallel to a longer edge of the test strip.

As will be outlined in further detail below, the analytical device may be a test element for detecting one or more analytes in a fluid, such as in a body fluid. The test element, such as the test strip, may be based on various detection techniques. Thus, as an example, the test element may be an optical test element, making use of an optical detection reaction for detecting the at least one analyte, e.g. by providing one or more detection or test chemicals capable of performing an optical detection reaction. Additionally or alternatively, the test element may fully or partially be embodied as an electrochemical test element, in which the at least one analyte can be detected by one or more electrochemical or electrical measurements. These types of test elements, both electrochemical and optical test elements, generally are known to the skilled person, specifically in the field of diabetes management and/or in the field of measurement of other parameters of a sample, such as coagulation parameters.

The process can comprise the following steps, which may be performed in the given order. Still, a different order of the process steps is feasible. Further, the process may comprise one or more additional process steps which are not listed in the following. Further, one, more than one or even all of the process steps may be performed repeatedly and/or continuously. Further, the process steps may be performed in a timely overlapping fashion and/or in parallel or simultaneously. Thus, as outlined above, the process specifically may be embodied as a continuous process. Consequently, one, more than one or even all of process steps, as outlined in further detail below, may be performed repeatedly or even continuously, at least over a period of time of at least 10 seconds, preferably of at least 1 minute or even over a period of time of 30 minutes or more. Thus, specifically, in a continuous process, a large number of the analytical devices may be produced subsequently, in a continuous fashion.

The process steps can be as follows: providing at least one carrier layer; providing at least one spacer layer; applying the spacer layer on top of the carrier layer; providing at least one cover layer; and applying the cover layer on top of the spacer layer. The process can further comprise at least one cutting step, i.e. one cutting step or, preferably, two or more cutting steps, wherein at least one capillary channel of the capillary element is cut out from the spacer layer.

As used herein, the term "providing" can generally refer to a step of making a specific element available to the process. The providing may take place in a continuous way, such as by providing one or more or even the entire carrier layer, the spacer layer and the cover layer in a continuous way, such as from one or more reels. Other types of providing are feasible. Further, the term "providing" may imply providing commercially available products or intermediate products or may imply a full or partial manufacturing of the products or intermediate products to be provided.

As further used herein, the term "carrier layer" can generally refer to a layer which can be capable of carrying one or more additional elements. The carrier layer, as will be outlined in further detail below, may be a web or tape. Other types of carrier layers are feasible. The carrier layer may be a flexible or deformable carrier layer, such as a foil. Further, the carrier layer itself may comprise one or more layers. Thus, the carrier layer itself may contain a carrier layer setup having a plurality of layers, such as a laminate. The carrier layer, as an example, may contain one or more plastic materials. The carrier layer, as will be outlined in further detail below, may be provided as a carrier layer tape, such as from a reel.

The carrier layer may contain further elements. Thus, the carrier layer itself may be a patterned carrier layer, having one or more patterned structures therein and/or on top. Thus, as outlined in the context of the prior art above, the analytical device may be an electrochemical analytical device, having a plurality of electrodes. The electrodes may be deposited, fully or partially, on the carrier layer, in a patterned fashion. Thus, the carrier layer may contain and/or may carry a plurality of patterned electrodes.

As further used herein, the term "spacer layer" can generally refer to an intermediate layer which can be, directly or indirectly, interposed in between the carrier layer and the cover layer and which can be capable of forming side walls of the capillary element. Thus, generally, the capillary element, specifically the capillary channel of the capillary element, may be formed by the carrier layer as a bottom, by the spacer layer providing the side walls of the capillary channel, and by the cover layer providing a top wall of the capillary channel.

Thus, the spacer layer generally may be or may comprise an arbitrary element which, at least after the cutting step, may provide side walls of the capillary channel of the capillary element. The spacer layer may be provided, before the cutting step, as a continuous spacer layer, such as by providing the spacer layer as a spacer layer tape. Other types of spacer layers are feasible.

The spacer layer, as an example, may be provided from a spacer layer supply reel, such as by providing one or more spacer layer tapes and/or one or more spacer layer foils. Thus, the spacer layer, as an example, may be a flexible and/or deformable element such as one or more spacer layer foils. As an example, the spacer layer may contain one or more plastic foils. Additionally or alternatively, the spacer layer may be or may comprise one or more adhesive layers. Thus, the step of applying the spacer layer on top of the carrier layer may comprise one or more steps of providing an adhesive layer to the carrier layer. Therein, liquid adhesives, adhesive pastes and/or solid adhesives may be used. As an example, liquid adhesives and/or adhesive pastes may be applied by one or more liquid application processes, such as one or more of a dispensing process, a coating process, a doctor blading process, a slot coating process, a printing process or any combinations thereof. In case a liquid adhesive is used, the process may imply one or more drying and/or curing steps in which the liquid adhesive and/or the adhesive paste can be fully or partially cured, such as by application of heat and/or ultraviolet radiation. Several techniques are feasible.

The spacer layer may comprise, itself, a plurality of layers, such as by providing the spacer layer in the form of a laminate spacer layer. Additionally or alternatively, as will be outlined in further detail below, the spacer layer may contain one or more layers of adhesive, on one side or on both sides. Thus, on a side facing the carrier layer, the spacer layer may contain an adhesive layer. Additionally or alternatively, on a side facing the cover layer, the spacer layer may contain a second adhesive layer. Thus, as an example, the spacer layer may be or may comprise a one-sided or a double-sided adhesive tape. Alternatively, one or more additional adhesive layers may be interposed in between the carrier layer and the spacer layer and/or in between the spacer layer and the cover layer, such as in one or more separate process steps.

As further used herein, the term "cover layer" can generally refer to an element which may provide a cover of the analytical device, thereby providing a top wall of the capillary channel of the capillary element. Again, the cover layer may be or may comprise a single cover layer or may comprise a plurality of cover layers or a plurality of parts or elements forming the cover layer. Thus, as for the carrier layer, the cover layer may, besides the functionality of covering the capillary channel, provide one or more analytical functions. Thus, as will be outlined in further detail below, the cover layer may comprise one or more analytical detection films. The cover layer itself may comprise one or more elements which may be positioned on top of each other or next to each other on top of the spacer layer. In the latter case, the cover layer may comprise a plurality of regions covering different regions of the spacer layer. Thus, the cover layer may comprise strip-shaped cover layers which may be located next to each other on top of the spacer layer. Additionally or alternatively, the cover layer may, itself, comprise a multi-layer setup, such as one or more laminates. The cover layer, as an example, may contain one or more flexible and/or deformable materials, such as one or more foils. As for the carrier layer and/or the spacer layer, the cover layer, as an example, may contain one or more plastic materials.

The carrier layer, the spacer layer and the cover layer, generally, may each have a suitable thickness. As an example, the carrier layer may have a thickness of 100 µm to 1 mm, preferably of 300 µm to 500 µm, such as 350 µm. The spacer layer, as an example, may have a thickness of 50 µm to 300 µm, specifically 80 µm to 150 µm and more specifically 100 µm. The cover layer, as an example, may have a thickness of 50 µm to 300 µm, such as 100 µm to 200 µm, specifically 50 µm. As outlined above, the carrier layer, the spacer layer and the cover layer each may be provided as tapes or webs, such as from respective supply reels. As an example, the carrier layer, the spacer layer and the cover layer may be provided as tapes which, independently, may have a length in the range of 5 mm to 70 mm, such as in the range of 10 mm to 50 mm. As further outlined above, the carrier layer, the spacer layer and the cover layer, independently, may contain plastic materials. Thus, as an example, the carrier layer and/or the cover layer may contain one or more of a polyester material, a polyethylene terephthalate or other materials. The spacer layer, as outlined above, may comprise one or more double-sided adhesive tapes.

As used herein, the term "applying", when referring to an application of one layer on top of another layer, can generally refer to positioning one layer on top of another layer and, optionally, securing or fastening the respective top layer to the respective bottom layer, such as fastening the spacer layer to the carrier layer or vice versa or fastening the cover layer to the spacer layer or vice versa. The latter step, i.e. fastening or fixing the respective top layer to the respective bottom layer, as an example, may imply a gluing or melting process, such as by using one or more adhesives and/or by using one or more lamination processes or heat-bonding processes. Thus, the spacer layer may be bonded to the carrier layer by one or more of an adhesive, a lamination or a heat-bonding or vice versa, and/or the cover layer may be bonded to the spacer layer or vice versa, by using one or more of an adhesive, a lamination and a heat-bonding. Other embodiments are feasible.

Further, as used herein, the term "on top of" can generally refer to the fact that one element can be located or placed on the other element, in a direction which may be defined as a "top direction", without restricting the possibilities of orienting this top direction in space. Thus, the top direction generally may be an arbitrary direction in space, such as an upward direction in space. Thus, the fact that the spacer layer can be applied on top of the carrier layer and the cover layer can be provided on top of the spacer layer can simply refer to the fact that the analytical device contains, in the given order, the carrier layer, the spacer layer and the cover layer, directly applied to one another, with these elements being in close contact, or with the possibility of interposing one or more elements in between the carrier layer and the spacer layer and/or in between the spacer layer and the cover layer.

As generally used herein, the term "cutting step" can refer to a step of applying a mechanical cutting tool to an element, thereby generating one or more cutting lines and/or thereby separating one or more first regions of the element to be cut from one or more second regions. The cutting step, therefore, may comprise one or more of a blade cutting, a stamping, an embossing, a punching or any other type of cutting or mechanical interaction with the element to be cut.

As further used herein, the term "capillary channel", as outlined above in the context of the capillary element, can generally refer to an arbitrary channel which can be capable of providing capillary forces to a fluid applied to the capillary element. The capillary channel, in the process disclosed above, can be formed within the spacer layer, wherein the spacer layer provides side walls of the capillary channel. The carrier layer and the cover layer, respectively, can provide bottom and top walls of the capillary channel. The capillary channel, thus, may simply be formed by a slit or a groove penetrating the spacer layer from a top side of the spacer layer to a bottom side of the spacer layer, thereby forming side walls of the capillary channel. As an example, the capillary channel may have a width in the range of 200 µm to 3 mm, preferably 400 µm to 1.5 mm.

In order to overcome the above-mentioned problems and technical challenges, the cutting step, as proposed herein, can be performed by using at least two cutting tools. The cutting tools can be complementing one another to form a contour of the capillary channel.

As used herein, the term "cutting tool" can generally refer to an arbitrary tool adapted for performing the above-mentioned cutting step. Thus, a cutting tool generally may be an arbitrary tool adapted for providing a cutting line and/or for providing a punching, an embossing, a stamping or any other type of cutting process. As will be outlined in further detail below, the cutting tool generally may be a kiss-cut-cutting tool.

As proposed above, at least two cutting tools are used. The at least two cutting tools, as an example, may comprise at least one first cutting tool and at least one second cutting tool, wherein the first cutting tool and the second cutting tool, as an example, can be fully or partially independent from one another and/or may be, for example, individually controllable. Thus, the cutting processes provided by the at least two cutting tools, as an example, can be independent with regard to their respective cutting processes, such as with regard to the timing of the exertion of the cutting action onto the element to be cut, i.e. onto the spacer layer. Further details with regard to potential embodiments of the cutting tools will be outlined below.

The cutting tools can complement one another to form a contour of the cutting channel. Thus, by the cutting tools, a contour of the cutting channel can be cut out from the spacer layer. Thereby, as an example, side walls of the capillary channel may be produced by such a cut. As used herein, the term "complementing one another to form a contour of the capillary channel" can generally refer to the fact that a capillary channel, i.e. one and the same capillary channel, can be cut by using the at least two cutting tools rather than using a single cutting tool. Thus, a first portion of the capillary channel, such as a first side wall or a portion of a first side wall, may be cut by a first cutting tool, and at least one second portion of the capillary channel, such as a second side wall, e.g. a second side wall opposing the first side wall, or a portion thereof, may be cut by using at least one second cutting tool, which, as an example, may be controlled individually from the first cutting tool. The at least two cutting tools, in combination, can provide the full contour of the capillary channel, i.e. can provide the contour of the part of the capillary channel which can be formed by the spacer layer. As used herein, the term "contour" can generally refer to a boundary of a geometric footprint of the capillary channel within the spacer layer, such as the boundary of the part of the capillary channel formed within the spacer layer. Thus, as an example, the contour of the capillary channel may be a projection of the side walls of the capillary channel into a plane parallel to a lateral extension of the capillary channel and/or may be a boundary line of a cross-section of the capillary channel in the plane of the spacer layer.

The at least two cutting tools, as outlined above, may comprise at least one first cutting tool and at least one second cutting tool. Thus, the at least two cutting tools may comprise at least two, at least three or even more cutting tools. In an embodiment, two cutting tools can be used. The cutting tools, each, may comprise a cutting edge, such as a blade or any other cutting element, and at least one basis, such as a flat, curved or even cylindrical basis, which can hold and actuate the at least one cutting edge. The bases of the at least two cutting tools, as an example, may be independent bases, such that the at least one first cutting tool can comprise at least one first basis and the at least one second cutting tool can comprise at least one second basis.

As outlined above, the cutting tools each, independently, may comprise a stamping and/or embossing tool. As an example, the cutting tools, each independently from each other, can comprise rotating cutting tools. Thus, the cutting tools, or one or more of the cutting tools, may comprise at least one cutting cylinder having at least one cutting edge. Thus, the cutting cylinder may comprise a cylindrical basis and at least one cutting edge protruding from the cylindrical basis. Thus, generally, a rotating cutting tool can refer to a cutting tool which can be capable of rotating, such as around a cylinder axis, and which can comprise at least one cutting edge, which, during the rotation process, can engage the object to be cut iteratively. Specifically, as outlined above, the at least two cutting tools may comprise at least one cutting cylinder having at least one cutting edge. More specifically, each of the cutting tools may comprise at least one cutting cylinder having at least one cutting edge. The cutting tools may further comprise at least one counter cylinder interacting with the at least one cutting cylinder. Thus, each of the cutting tools may comprise at least one counter cylinder, or two or more cutting tools may share at least one common counter cylinder. Thus, the spacer layer to be cut may be led through a calender nip between the cutting cylinder and the counter cylinder. Thus, each of the cutting tools may comprise a cutting cylinder and, thus, may have a calender nip between the respective cutting cylinder and the counter cylinder, such that at least two calender nips can be provided, one calender nip for each of the cutting tools, wherein the spacer layer can be led through the calender nips subsequently.

The at least two cutting tools each may comprise at least one cylinder pair, each cylinder pair comprising at least one cutting cylinder and at least one counter cylinder. Therein, as outlined above, separate counter cylinders may be used for the cutting tools. Alternatively, two or more cutting tools may share a common counter cylinder. Thus, a common counter cylinder may be provided for at least two of the cutting tools, the common counter cylinder interacting with two or more cutting cylinders. Thus, a first cutting cylinder may be provided by a first cutting tool, and a second cutting cylinder may be provided by a second cutting tool, wherein the first cutting cylinder and the common counter cylinder form a first cylinder pair, and wherein the second cutting cylinder and the common counter cylinder form a second cylinder pair. The common counter cylinder, as an example, may rotate at a constant rotational speed, wherein the cutting cylinders of the cutting tools interacting with the common counter cylinder may be individually controllable or controlled. Thus, specifically, the at least one first cutting tool may comprise at least one first cutting cylinder, and the at least one second cutting tool may comprise at least one second cutting cylinder, wherein the first cutting cylinder and the second cutting cylinder may be individually controllable, specifically with regard to their rotational speed.

In case the cutting tools comprise at least one cutting cylinder, the cutting cylinder, as outlined above, may comprise a cylindrical basis and one or more cutting edges protruding from the rotational basis. Therein, the cutting cylinder may contain a plurality of cutting edges located on a circumferential surface of the cutting cylinder, specifically of a cylindrical basis of the cutting cylinder. These cutting edges may be spaced, in a circumferential direction, equidistantially.

Further embodiments relate to the cutting edges. Thus, the cutting edges generally may be S-shaped. Other shapes, however, are feasible. The S-shapes may be round S-shapes or angled S-shapes. The S-shapes may specifically be elongated S-shapes. Further, both the at least one first cutting tool and the at least one second cutting tool may provide cutting edges having S-shapes, wherein the S-shape of the at least one first cutting tool may be oriented in an opposite direction as compared to the S-shape of the at least one second cutting tool.

The cutting edges may have an elongated shape, following the elongated shape of the at least one capillary channel. The cutting edges may be oriented essentially perpendicular to a transportation direction of the spacer layer.

Generally, as used herein, the term "essentially perpendicular" can refer to the fact that a perpendicular orientation may be preferred. However, slight deviations from a perpendicular orientation may be feasible, such as orientations which can deviate from a perpendicular orientation by no more than approximately 10 degrees, preferably by no more than about 5 degrees. Similarly, when referring to an "essentially parallel orientation", this term can be used to indicate that a parallel orientation may be preferred, wherein deviations from a parallel orientation can be feasible, such as deviations by no more than approximately 10 degrees, preferably by no more than about 5 degrees.

As further used herein, a "direction of transportation" can generally refer to the fact that a continuous process can be used, wherein the respective element, the transportation direction of which is referred to, can be transported with regard to the at least one cutting tool. Thus, the transportation direction of the spacer layer can generally refer to the fact that a continuous process may be used in which the spacer layer can be moved or transported with regard to the at least two cutting tools, wherein the transportation direction can be the local transportation direction of the spacer layer at the position of the respective cutting edge. Thus, specifically, the cutting edges may have an elongated shape, such as by using cutting edges of an elongated S-shape. The backbone of the S-shape may form a direction of orientation of the cutting edge, wherein this direction may be oriented essentially perpendicular to the transportation direction of the spacer layer.

The cutting edges of the at least two cutting tools specifically may have a mirror symmetry. Thus, when projecting a cutting edge of at least one first cutting tool and a cutting edge of at least one second cutting tool into a common plane, the cutting lines or projections of these cutting edges may be mirror-symmetrical. Specifically, as outlined above, this symmetry may be realized by using an S-shape for a first one of the cutting edges, and by using an inverted S-shape for at least a second one of the cutting edges.

The process specifically may be performed by using at least one inspection tool. The inspection tool may be used for detecting cutting lines generated by one or both of the cutting tools. The inspection tool may be an arbitrary tool for detecting one or more cutting lines. As an example, the inspection tool may comprise at least one optical inspection tool, such as at least one camera, such as in conjunction with at least one image recognition system. One or more inspection tools may be used. Therein, the at least one inspection tool may be used for detecting at least one cutting line generated by a first cutting tool and/or an at least one inspection tool may be used for detecting at least one cutting line generated by at least one second cutting tool. Further, the process may make use of at least one control device, for controlling at least one of the cutting tools in accordance with a result provided by the inspection tool. Thus, the result may provide an actual value, such as an actual value of a position of one or more cutting lines generated by one or more of the cutting tools, and the actual value, in the control device, may be compared with at least one given value. At least one control device may be adapted to control the at least one cutting tool and/or one or more of the cutting tools, in accordance with this comparison.

Further, at least one of the cutting tools, such as a first cutting tool, may be adapted for generating at least one separation line in the spacer layer, for separating neighboring analytical devices in a continuous process, specifically at least one perforation line. Thus, a straight perforation line, containing a plurality of neighboring perforations, may be oriented essentially perpendicular to a direction of transportation of the spacer, in order to allow for, later on, separating the analytical devices in the above-mentioned individualization step. Thus, at least one of the cutting tools may provide an additional cutting edge and/or blade, for generating the at least one perforation line.

Further embodiments can refer to the order of the above-mentioned process steps. Thus, cutting may at least partially be performed after applying the spacer layer on top of the carrier layer. In other words, the spacer layer may fully or partially be cut when applied on top of the carrier layer. Additionally or alternatively, cutting may fully or partially be performed before applying the spacer layer on top of the carrier layer. In other words, the spacer layer may be cut fully or partially before applying the spacer layer to the carrier layer. In the latter case, the spacer layer, during the cutting step, may be a stand-alone layer or may be applied to at least one supporting element. Thus, as an example, during the cutting step, the spacer layer may be located on top of at least one support tape, wherein, after cutting, the support tape may be removed, and the spacer layer can be applied on top of the carrier layer.

Further embodiments relate to the cutting process itself. Thus, each of the cutting tools may generate at least one cutting line within the spacer layer. As used herein, the term "cutting line" can generally refer to a separation line which can separate at least one first portion of the spacer layer from at least one second portion of the spacer layer. Since at least two cutting tools are used, each of the cutting tools can generate at least one cutting line. The cutting lines generated by the cutting tools may overlap in at least one overlapping region of the spacer layer. As used herein, the term "overlap" can generally refer to the fact that the cutting lines generated by the at least two cutting tools can differ in at least one point, line or region and can be identical in at least one point, line or region. Thus, as an example, the cutting lines generated by the different cutting tools can be overlapping by crossing each other in the at least one overlapping region. Thus, the at least one overlapping region may comprise at least one crossover of the cutting lines generated by the at least two cutting edges. By generating an overlapping region, positioning tolerances of the cutting tools with respect to one another may be compensated for in order to avoid the situation that the cutting lines generated by the cutting tools fail to fully complement one another and, thus, incomplete borderlines of the capillary channel can be formed.

One or more overlapping regions of the cutting lines may be feasible. Thus, the capillary channel may comprise at least one application region for applying at least one sample to the capillary element and at least one end region located at an end of the capillary element opposing the application region, wherein the overlapping region at least partially can be located in the end region. One or more additional overlapping regions may be located in other positions, such as close to the application region.

The cutting lines generated by the cutting tools specifically may be mirror-symmetric, as outlined above. An axis of symmetry specifically may be oriented essentially perpendicular to a transport direction of the spacer layer.

The cutting step may be performed such that, as outlined above, the cutting tools can be individually controlled. The control may take place individually, with regard to at least one cutting parameter. The at least one cutting parameter specifically may be selected from the group consisting of: a cutting speed, a rotational speed of at least one rotating cutting tool, a cutting frequency of a periodic cutting, a phase shift of a periodic cutting, a cutting position, a distance between two cutting cylinders, a transportation velocity of the spacer layer. Other cutting parameters may be controlled additionally and/or alternatively, and combinations of the named cutting parameters to be controlled may be feasible.

The cutting tools each may individually be synchronized with at least one position of the spacer layer and/or a transportation speed of the spacer layer. Thus, as outlined above, the spacer layer may be transported and/or moved at the position of the respective cutting tool, and the respective cutting tool may be synchronized with the position of the spacer layer and/or a transportation speed of the spacer layer at the position of the respective cutting tool. The speed and/or position of the spacer layer may be recognized by using one or more positioning marks, such as one or more fiducial marks, and/or by using one or more perforations within the spacer layer. Thus, the spacer layer may be a perforated tape having a plurality of equidistantially spaced perforations at an edge of the tape which may function as positioning marks for detecting a position of the spacer layer and/or a transportation speed of the spacer layer. Additionally or alternatively, other types of marks may be used for recognizing the speed and/or position of the spacer layer, such as features which are present within the spacer layer and/or features which can be intentionally introduced into the spacer layer. Thus, as an example, markings produced by a laser and/or a printing technology may be applied. Additionally or alternatively, given features within the spacer layer may be used as markings, such as edges, e.g. cutting edges. Other possibilities are feasible.

Further embodiments can relate to the fact that the process may be embodied as a continuous process. Thus, a plurality of the analytical devices may be produced, such as sequentially. The carrier layer may provide at least one carrier element for each of the analytical devices, the spacer layer may provide at least one spacer element for each of the analytical devices, and the cover layer may provide at least one cover element for each of the analytical devices. Thus, the process may be a continuous tape process, and the process further may comprise at least one singulation step, wherein, in the singulation step, the analytical devices can be cut from a web containing the carrier layer, the spacer layer and the cover layer. The singulation step, as an example, may be performed after performing the other steps and the cutting step. The plurality of the analytical devices, as obtained by performing the singulation step, may be oriented essentially perpendicular to at least one transport direction of the web. The singulation step may contain an arbitrary process for separating the analytical devices from the web, such as a process of mechanical cutting, a process of laser cutting or any other process of cutting. The individualized analytical devices may be collected for further use and/or for further processing or packaging. The singulation step may be performed such that the capillary channel may be oriented essentially perpendicular to a transport direction of the web.

As outlined above, the process may be a continuous process. Thus, the process specifically may be a reel process, wherein the carrier layer can be provided as a continuous carrier tape, wherein the spacer layer can be provided as a continuous spacer tape and wherein the cover layer can be provided as a continuous cover tape. As used herein, the term "continuous" can generally refer to the fact that the respective tapes can have lengths sufficient for providing the respective elements for a plurality of the analytical devices. Thus, the respective tapes may have a length exceeding the width of the analytical element by at least a factor of 100, or by at least a factor of 1000 or by at least a factor of 10000. The tapes may be provided by using supply reels.

Further embodiments can relate to the capillary channel. Thus, the capillary channel may comprise at least two side walls. The at least two side walls, as an example, may be oriented essentially parallel to an axis of elongation of the analytical device. The at least two side walls may be oriented essentially parallel to one another. The side walls may be produced in the cutting step, wherein at least one first one of the side walls may be produced by a first one of the cutting tools, and at least one second one of the side walls may be produced by a second one of the cutting tools. The side walls, as an example, may be opposing side walls.

The process, as an example, may be performed by using positioning marks, in order to allow for a precise positioning of the cutting lines produced within the spacer layer by the at least two cutting tools. Thus, one or both of the carrier layer and the spacer layer may contain position marks. Thus, the carrier layer may contain carrier layer position marks, and/or the spacer layer may contain spacer layer position marks. These position marks simplify the cutting step, in order to allow for a precise positioning of the cutting lines with regard to the position of the carrier layer and/or the spacer layer. The position marks each, as an example, may comprise printed position marks, such as color markings, and/or may contain perforations. Thus, as outlined above, the carrier layer may be a continuous carrier layer tape embodied as a perforated carrier layer tape having a continuous row of holes, such as at an edge of the carrier layer tape. Additionally or alternatively, the spacer layer tape may be embodied as a perforated spacer layer tape, such as having a row of perforation holes at an edge of the spacer layer tape. The application of the spacer layer on top of the carrier layer and/or the cutting step may be performed in a controlled fashion, such as in a position-controlled fashion, in order to precisely position the cut or uncut spacer layer on top of the carrier layer and/or in order to precisely control the positioning of the cutting step with regard to the position of the carrier layer and/or the position of the spacer layer. Thus, the cutting lines generated by the at least two cutting tools may be individually or commonly controlled with regard to a position of the carrier layer and/or a position of the spacer layer.

Further embodiments can relate to the application of the spacer layer on top of the carrier layer, i.e. the application of the spacer layer onto the carrier layer. Thus, in the applying the spacer layer on top of the carrier layer, the spacer layer may be one or both of glued to the carrier layer, by using an adhesive process, and/or laminated onto the carrier layer, such as by using one or both of a heat and/or pressure lamination. Similarly, in the applying the cover layer on top of the spacer layer, the cover layer may be one or both of glued to the spacer layer and/or laminated onto the spacer layer. In case a plurality of cover layers is used, such as by using several cover layer elements, a combination of processes might be used.

The spacer layer, as outlined above, may comprise at least one adhesive tape. The adhesive tape generally may be a one-sided adhesive tape or, as an example, a double-sided adhesive tape. The adhesive tape may contain one or two adhesive sides. Before applying the spacer layer to the carrier layer and/or before applying the cover layer to the spacer layer, at least one liner element may be removed from the adhesive side.

The spacer layer, the carrier layer and the cover layer, individually and independently, may be made of at least one plastic material. Thus, for potential plastic materials to be used, reference may be made to the possibilities listed above.

Further embodiments refer to the cutting step. The cutting step may contain at least one step of removing parts of the spacer layer which are not required to form the at least one capillary element, specifically the parts which correspond to the at least one capillary channel of the capillary element. Thus, in the cutting step, an inner part of the capillary channel, which may be unwanted and may not form part of the analytical device to be produced, may be separated from a remainder of the spacer layer, such as a remainder of the spacer layer which, later on, forms the walls of the at least one capillary channel. The inner part subsequently or simultaneously may be removed from the carrier layer and, as an example, may be disposed of. This step of removing the inner part may be part of the cutting step itself and/or may be performed in a subsequent step. As an example, the removal of the inner part, i.e. the part which is not required within the spacer layer, may be performed in a continuous process. The inner part, as an example, may be removed from the carrier layer by delamination. Thus, the inner part may be pulled off from the carrier layer. In case a continuous process is performed, i.e. in case a plurality of the analytical devices is produced in a continuous process, such as subsequently, the inner parts of the plurality of the analytical devices may be removed in a continuous process, such as sequentially. Thus, the inner parts of the plurality of the analytical devices may be removed in a continuous web process, by continuously pulling off a waste web containing the inner parts.

Further embodiments can relate to the cover layer. Thus, the cover layer may comprise an analytical detection film. As used herein, an analytical detection film generally can be a film having analytical properties, i.e. a film which may be used for analysis of at least one sample, such as for detecting at least one analyte in the sample and/or for detecting at least one property of the sample.

Thus, the detection film may comprise at least one detector material, the detector material adapted to perform at least one detection reaction in the presence of an analyte to be detected. Therein, the term "analyte" can be interpreted in a broad sense. Thus, as outlined above, the analyte, as an example, may contain an arbitrary substance, compound or mixture of substances which can be part of the metabolism of a human or animal user. Thus, the analyte itself may be a metabolite. Alternatively, the analyte may be or may contain another type of parameter of the sample, such as a coagulation parameter. The detector material generally can be a material, such as a single material or a compound of materials or a mixture of materials, which can be adapted such that at least one detectable parameter of the detector material can change due to the detection reaction. As outlined above, the detectable parameter may be an arbitrary parameter which can be detectable in a biological, physical or chemical process. As an example, the at least one detectable parameter can be at least one of an electrochemical parameter, such as an electrical parameter, and an optical parameter, such as a color, a fluorescence property and/or a reflectivity and/or remission property.

Thus, the detector material may be an electrochemical detector material adapted for electrochemical detection reactions and/or an optical detector material adapted for optical detection reactions. These types of materials generally are known to the skilled person, such as in the field of glucose measurements. Thus, as an example, the at least one detector material may contain at least one enzyme adapted for performing at least one enzymatic reaction with the at least one analyte to be detected, wherein the at least one enzymatic reaction can be detectable by using at least one dye and/or by using at least one electrochemical measurement process, i.e. a process for detecting changes of electrical potentials and/or electrical charges and/or electrical voltages or currents. Thus, in the latter case, the analytical device may comprise one or more electrodes, such as one or more electrodes provided on top of the carrier layer, in between the carrier layer and the spacer layer, and/or one or more electrodes applied to the cover layer, on the side of the cover layer facing towards the spacer layer. The one or more electrodes, fully or partially, may be in contact with the at least one detector material. Further, the one or more electrodes may comprise one or more electrode areas facing towards an interior side of the at least one capillary element. Further, the one or more electrodes each may comprise one or more contact leads and/or contact wires for electrically contacting the electrodes.

The detection film may comprise a layer setup, the layer setup having at least one detection layer having the detector material. The layer setup may be a one-layer setup, having the detection layer only. Alternatively, the layer setup may be a multi-layer setup, having at least one additional layer. As an example, the at least one additional layer may be or may comprise at least one additional layer above or beneath the detection layer. Thus, at least one additional layer may be interposed in between the detection layer and the capillary element and/or may be interposed in between the detection layer and the carrier layer. The additional layer, as an example, may be at least one of a white pigment layer, such as for providing a white background for optical measurements, and/or a removal layer, for removing particulate components of a sample. These layer setups generally are known to the skilled person, specifically in the field of glucose measurements in whole blood.

As outlined above, the analytical device may be an arbitrary analytical device for analytical measurements. The analytical device specifically may be an analytical test element adapted for determining at least one parameter of a sample applied to the analytical device, such as at least one physical, chemical or biological parameter or any combination thereof. As an example, the at least one parameter may be a concentration of at least one analyte contained in the sample.

The analytical device, as an example, may be selected from the group consisting of a test strip and a test tape. Thus, as an example, the analytical device may be a strip-shaped analytical device, having a thickness of 0.2 mm to 3 mm, a width of 2 mm to 15 mm, and a length of 15 mm to 60 mm. Other embodiments are feasible.

A production device for the production of at least one analytical device is proposed. The production device, as an example, may be designed as a production device for a continuous production process, such as for a continuous tape process, for subsequently producing a large number of analytical devices. The production device comprises: at least one carrier layer supply device for providing at least one carrier layer; at least one spacer layer supply device for providing at least one spacer layer; at least one spacer layer application device for applying the spacer layer on top of the carrier layer; at least one cover layer supply device for providing at least one cover layer; and at least one cover layer application device for applying the cover layer on top of the spacer layer.

The production device can further comprise at least two cutting tools, such as at least one first cutting tool and at least one second cutting tool. The production device can be adapted for cutting out at least one capillary channel of the capillary element from the spacer layer by using the cutting tools. The cutting tools can be complementing one another to form a contour of the capillary channel.

As used herein, a carrier layer supply device can be a generally arbitrary device for supplying a carrier layer. As an example, the carrier layer supply device can be a supply device for supplying at least one carrier layer tape, such as a supply device having a carrier layer supply reel. Further, the carrier layer supply device may comprise at least one transport device for transporting the carrier layer, such as one or more reels and/or one or more transport drums or cylinders for transporting the carrier layer.

Similarly, a spacer layer supply device may be an arbitrary device for providing a spacer layer, such as in an uncut fashion and/or, after the cutting process, in a cut fashion. Thus, as an example, as for the carrier layer supply device, the spacer layer supply device may comprise at least one spacer layer supply device adapted for providing a spacer layer as a spacer layer tape. As an example, the spacer layer supply device may comprise at least one spacer layer supply reel. Further, the spacer layer supply device may comprise one or more spacer layer transport devices, such as one or more transport drums and/or one or more transport cylinders.

As further used herein, the spacer layer application device generally may be an arbitrary device adapted for applying the spacer layer on top of the carrier layer. Thus, the spacer layer application device simply may comprise a positioning device for positioning the spacer layer on top of the carrier layer. Additionally or alternatively, the spacer layer application device may be a device for connecting the spacer layer and the carrier layer, such as an application device adapted for exerting pressure and/or heat to one or both of the spacer layer and the carrier layer, in order to mount the spacer layer to the carrier layer or vice versa. Thus, the spacer layer application device may comprise at least one device for laminating the spacer layer to the carrier layer. The lamination device, as an example, may comprise at least one calender nip. These types of application devices generally are known to the skilled person. Additionally or alternatively, the at least one spacer layer application device may comprise one or more additional application devices, such as one or more additional devices for applying one or more adhesives to the spacer layer and/or the carrier layer, before combining the spacer layer and the carrier layer.

As for the carrier layer supply device and for the spacer layer supply device, the at least one cover layer supply device generally may be an arbitrary device for supplying the at least one cover layer. Thus, the cover layer supply device, as an example, may be a tape supplying device for supplying one or more cover layer tapes. Thus, again, the at least one cover layer supply device may comprise one or more cover layer supply reels, for supplying one or more cover layer tapes. Further, the at least one cover layer supply device may comprise one or more transport devices, such as one or more transport drums and/or transport cylinders, for transporting the cover layer.

As for the at least one spacer layer application device, the at least one cover layer application device generally may be an arbitrary device for applying the cover layer on top of the spacer layer and, optionally, for mounting the cover layer onto the spacer layer. Thus, again, the cover layer application device generally may be a device for aligning the cover layer onto the spacer layer. Additionally or alternatively, the cover layer application device may be adapted for mounting the cover layer onto the spacer layer, such as by exerting pressure and/or heat. Again, the cover layer application device may be a lamination device, such as a lamination device having one or more calender nips. Further, as for the at least one spacer layer application device, the at least one cover layer application device may have an additional adhesive application device, adapted for applying adhesive onto the spacer layer and/or onto the cover layer, before applying the cover layer on top of the spacer layer.

It can be noted that one or more of the devices named above also may fully or partially be combined in a common device. Thus, the at least one carrier layer supply device, the at least one spacer layer supply device and the at least one cover layer supply device may fully or partially be combined in a common supply device adapted for providing the at least one carrier layer, the at least one spacer layer and the at least one cover layer. Additionally or alternatively, the at least one spacer layer application device and the at least one cover layer application device may fully or partially be combined in a common application device. Thus, as an example, a common lamination device, specifically a common calender, may be provided, for simultaneously mounting the spacer layer onto the carrier layer and for mounting the cover layer onto the spacer layer. This combination may be performed fully or partially. In the latter case, as an example, the spacer layer application device may comprise at least one spacer layer positioning device for positioning the spacer layer on top of the carrier layer, and, independently, the at least one cover layer application device may comprise at least one cover layer positioning device for positioning the cover layer on top of the spacer layer. Additionally, in a combined fashion, both devices may additionally comprise a common lamination device, for laminating the sandwich setup comprising the carrier layer, the spacer layer and the at least one cover layer. Other embodiments are feasible.

As outlined above, the production device can further comprise at least two cutting tools. For potential setups and embodiments of the at least two cutting tools, reference may be made to the description of the process as given above and/or to one or more of the embodiments disclosed in further detail below.

Generally, the production device may be adapted to perform the production process according to any one of the embodiments of the production process disclosed above and/or according to any one of the embodiments given in further detail below.

An analytical device producible by the process according to the present disclosure is disclosed. For potential embodiments of the analytical device, reference may be made to the disclosure of the process as given above or as given in further detail below. Thus, the analytical device may be an analytical test element, such as a test element for detecting at least one analyte in a fluid sample, for example a test element for detecting at least one analyte in a fluid sample, such as in a sample of a body fluid. The advantages of the process, as will be given in further detail below, can also apply to the analytical device, since the at least one capillary channel of the at least one capillary element of the analytical device may be smaller with regard to a minimum width of the capillary channel, and a high precision of the width of the capillary channel and/or a high precision of the position of the capillary channel within the analytical device may be maintained.

The fact that the process according to the present disclosure can be used for manufacturing the analytical device, including the use of at least two cutting tools complementing one another for cutting out the contour of the capillary channel, may easily be detected by visually inspecting the analytical device. Thus, specifically in a region in which cutting lines generated by the at least two cutting tools join or even overlap one another, the complementing fashion of the cutting process may be detected by simple visual inspection. Thus, specifically in case the cutting lines are overlapping one another, the analytical device as producible by the process according to the present disclosure can be clearly distinct from analytical devices manufactured by traditional cutting processes.

The process, the production device and the analytical device according to the present disclosure can provide a large number of advantages over known processes, production devices and analytical devices. Thus, the contour of the at least one capillary channel can be cut in complementing fashion, by using the plurality of cutting tools. Thus, each cutting tool can provide a part of the contour of the capillary channel, only, such as only a part of a circumferential rim of the capillary channel. Thereby, an individual control of these parts, i.e. an individual control of the cutting lines provided by each of the cutting tools, can be possible. Further, the same disadvantages and challenges of known techniques may be avoided, specifically with regard to a minimum width of the capillary channel. Thus, by using at least two cutting tools, such as at least two cutting tools being offset from one another in the transport direction of the web and/or of the spacer layer, the interior part of the capillary channel may not get caught in between two cutting edges of one and the same cutting tool, as in previously known techniques. Consequently, a squeezing of spacer material, such as tape material, adhesives or other spacer materials, in between cutting edges or blades of one and the same cutting tool may be avoided, leading to a clean cut of the capillary channel. Consequently, since this squeezing of spacer material may be avoided, residuals of spacer material within the capillary elements may be avoided or at least reduced. Therefore, surface properties and capillary properties of the at least one capillary element may be improved as compared to traditional manufacturing techniques.

As a further advantage, improved control of the cutting process may be named. Thus, due to the possibility of individually controlling the cutting tools, the divisor of the analytical device, i.e. the ratio of the width of the capillary channel and the width of the analytical device, may be chosen, adjusted or controlled precisely. The divisor generally can be a geometric parameter of the analytical device which can denote a ratio of the capillary width and the distance between neighboring capillaries. As will be evident and as will be outlined in further detail below, the divisor may be adjusted by corresponding process parameters, e.g. by controlling the at least two cutting tools. Thus, variable divisors can be possible. Further, continuously varying divisors or even divisors varying in a stepwise fashion may be manufactured, at a high yield. Additionally or alternatively, one or more of the capillary, the pitch, the width of the analytical device or a distance between neighboring capillary channels may be adjusted and/or controlled, independently from each other.

As an example, deviations of a width of the capillary channel from a given width or predetermined width may be compensated by changing a phase between the at least two cutting tools, thereby changing a timing of the cutting performed by these at least two cutting tools. Therein, one of the cutting tools may be used as a master cutting tool, and the other cutting tool may be synchronized with the master cutting tool, such as by using a controllable phase shift between the additional cutting tool and the master cutting tool. Alternatively, the at least two cutting tools may be synchronized with a master signal, such as by using an individually adjustable phase shift in between each cutting tool and the master signal. Therein, deviations of the width of the capillary channel from the given width may be adjusted by individually adjusting the phase shifts.

Consequently, since, assuming a constant distance between neighboring capillary channels, changing the width of the capillary channels can change the divisor, an adjustment of the divisor can be feasible.

Similarly, in case a misplacement of the capillary channel needs to be determined, an adjustment may be made by simultaneously or in equal measure adjusting the phases of the at least two cutting tools, such that a phase difference or phase shift between the at least two cutting tools can remain constant. Again, as for the example given above, one of the cutting tools may be used as a master cutting tool and the other one as a slave cutting tool. Therein, the phase of the master cutting tool may be adjusted to compensate for a misplacement of a first edge of the capillary channel, and the phase of the slave cutting tool may be adjusted by the same amount, thereby compensating for a misplacement of a second edge of the capillary channel. Thereby, the positioning of the capillary channel may be corrected, without changing the width of the capillary channel. Similarly, instead of using a master-slave-configuration, a master signal may be used, and the phase shifts of the at least two cutting tools as compared to the master signal may be increased or decreased by the same amount, thereby changing the position of the first and second edges of the capillary channel without changing the width of the capillary channel.

Further, the at least one cutting step may be performed both in a state in which the at least one spacer layer has been applied to the at least one carrier layer and/or before applying the spacer layer to the carrier layer. The first option, which also can be referred to as a kiss-cut-process, specifically draws benefit from the fact that a compression of interior material in between two cutting edges of one and the same cutting tool may be avoided. Additionally or alternatively, the cutting of the spacer layer may fully or partially be performed in a step in which the at least one spacer layer can be located on top of at least one support tape, wherein the support tape may be removed after the cutting step. The support tape often can be referred to as a transfer tape.

Specifically in the latter case, using a support or transfer tape, the supply and the cutting of the spacer layer may be performed in a separate process step, and the spacer layer, in a cut fashion, may be stored individually, before supplying the cut spacer layer and applying the spacer layer onto the carrier layer. The pre-manufactured and cut spacer layer may also contain markings for the individualization process, such as perforations indicating borderlines between neighboring analytical devices. Further, the pre-manufactured and cut spacer layers may be stored individually. The pre-manufactured spacer layers may, as outlined above, contain position markings, such as positioning perforations. As an example, rows of holes, such as holes produced at a rim of the spacer layers, may be present. The position markings may correspond to position markings in the carrier layer, such as corresponding holes in the carrier layer. Thereby, a mounting technique may be used in which the holes of the spacer layer are positioned on top of corresponding holes of the carrier layer. Thus, the production device in fact may comprise two independent production devices, wherein the cutting tools and the cutting step are performed by a first production device or sub-device, and wherein the actual manufacturing of the layer setup, comprising the carrier layer, the spacer layer (in a cut fashion) and the cover layer, can be performed in a second production device or a second sub-device. The production devices may be established as separate, independent machines, the first production device adapted for producing the capillary channel, and the second production device adapted for mounting the above-mentioned layer setup. Alternatively, the machines may be combined in an arbitrary fashion.

Further, a large number of advantages with regard to the precision of the manufacturing process and with regard to the possibility of controlling the cutting step can be provided. Thus, firstly, by avoiding the above-mentioned squeezing effect, clean and non-deformed cutting lines may be established. Further, a high flexibility with regard to the geometry of the capillary channel can exist. The width of the capillary channel and the distance between neighboring capillary channels, specifically in a direction of transport of the spacer layer, may be adjusted individually. Further, misplacements and deviations from a predetermined position of the cutting lines may be detected individually and may be adjusted by appropriate control means. Thus, the production device may comprise at least one inspection device, and the process may make use of an appropriate inspection device, for detecting deviations of the cutting lines generated by the individual cutting tools or from a predetermined given value or given position. This inspection device may comprise, for example, a simple camera which, for example, may be located downstream the cutting tools. By comparing the visual result of the inspection with one or more predetermined given values, a correction algorithm or control algorithm may be applied, and the at least two cutting tools may be controlled individually, such as with regard to the cutting speed and/or the timing of the cutting. Thereby, an accumulation of misplacements, which may occur during conventional processes, is detectable, and may quickly and simply be corrected for.

A process for the production of at least one analytical device with at least one capillary element is disclosed. The process can comprise providing at least one carrier layer and at least one spacer layer. The spacer layer can be applied on top of the carrier layer. At least one cover layer can be provided. The cover layer can be applied on top of the spacer layer. The process can further comprise at least one cutting step. At least one capillary channel of the capillary element can be cut out from the spacer layer. The cutting step can be performed by using at least two cutting tools. The cutting tools can complement one another to form a contour of the capillary channel.

The cutting tools comprise at least one rotating cutting tool. The cutting tools can comprise at least one cutting cylinder having at least one cutting edge. The cutting tools can further comprise at least one counter cylinder interacting with the cutting cylinder.

The spacer layer can be led through a calender nip between the cutting cylinder and the counter cylinder.

At least two cylinder pairs can be used in the cutting step. Each cylinder pair can form one of the cutting tools. Each cylinder pair can comprise at least one cutting cylinder and at least one counter cylinder. A common counter cylinder can be provided for the at least two cutting tools. The common counter cylinder can interact with a plurality of cutting cylinders. The common counter cylinder can rotate at a constant rotational speed. The cutting cylinders of the cutting tools interacting with the common counter cylinder can be individually controlled.

The cutting cylinder can contain a plurality of cutting edges located on a circumferential surface of the cutting cylinder. The cutting edges can be spaced equidistantially. The cutting edges can be S-shaped. The cutting edges can be oriented essentially perpendicular to a transportation direction of the spacer layer. The cutting edges of the at least two cutting tools can have a mirror symmetry.

In one embodiment, the cutting step can be at least partially performed after performing applying the spacer layer on top of the carrier layer. In another embodiment, the cutting step is at least partially performed before performing applying the spacer layer on top of the carrier layer.

During the cutting step, the spacer layer can be located on top of at least one support tape, wherein, after the cutting step, the support tape can be removed and the spacer layer can be applied on top of the carrier layer.

Each of the cutting tools can generate at least one cutting line within the spacer layer. The cutting lines generated by the cutting tools can overlap in at least one overlapping region.

The capillary channel can comprise an application region for applying at least one sample to the capillary element and at least one end region located at an end of the capillary element opposing the application region. The overlapping region at least partially can be located in the end region.

The cutting lines generated by the cutting tools can be mirror-symmetric.

An axis of symmetry can be oriented essentially perpendicular to a transport direction of the spacer layer.

The cutting tools can be individually controlled with regard to at least one cutting parameter. At least one cutting parameter can be selected from the group comprising of: a cutting speed, a rotational speed of a rotating cutting tool, a cutting frequency of a periodic cutting, a phase shift of a periodic cutting, a cutting position, a distance between two cutting cylinders, a transportation velocity of the spacer layer.

The cutting tools can be individually synchronized with at least one of a position of the spacer layer and a transportation speed of the spacer layer.

A plurality of the analytical devices can be produced. The carrier layer can provide at least one carrier element for each of the analytical devices. The spacer layer can provide at least one spacer element for each of the analytical devices. The cover layer can provide at least one cover element for each of the analytical devices.

The process can further comprise at least one singulation step. In the singulation step, the analytical devices can be cut from a web containing the carrier layer, the spacer layer and the cover layer. The plurality of the analytical devices can be oriented essentially perpendicular to at least one transport direction of the web. The capillary channel can be oriented essentially perpendicular to a transport direction of the web. The at least two cutting tools can be located offset from each other in the transport direction of the web.

The process is a reel process. The carrier layer can be provided as a continuous carrier tape. The spacer layer can be provided as a continuous spacer tape. The cover layer can be provided as a continuous cover tape.

The capillary channel can comprise at least two side walls. The side walls can be produced in the cutting step. At least a first one of the side walls can be produced by a first cutting tool. At least a second one of the side walls can be produced by a second cutting tool. The side walls can be opposing side walls. The side walls can be oriented essentially parallel to a longitudinal axis of the analytical device.

The carrier layer can contain a plurality of carrier layer positioning marks. The carrier layer positioning marks can contain perforations. The spacer layer can contain a plurality of spacer layer positioning marks. The spacer layer positioning marks can contain perforations. The spacer layer can be applied on top of the carrier layer in a position-controlled fashion by using one or both of carrier layer positioning marks within the carrier layer and spacer layer positioning marks within the spacer layer. The cutting step can be performed in a position-controlled fashion by using one or both of carrier layer positioning marks within the carrier layer and spacer layer positioning marks within the spacer layer.

In applying the spacer layer on top of the carrier layer, the spacer layer can be one or both of glued to the carrier layer or laminated onto the carrier layer. In applying the cover layer on top of the spacer layer, the cover layer can be one or both of glued to the spacer layer or laminated onto the spacer layer. The spacer layer can contain at least one adhesive tape. The adhesive tape can be a double-sided adhesive tape. The spacer layer can be fully or partially made of a plastic material. The carrier layer can be fully or partially made of a plastic material. The cover layer is fully or partially made of a plastic material.

In the cutting step, an inner part of the capillary channel can be separated from a remainder of the spacer layer. The inner part can be removed from the carrier layer. The inner part can be removed from the carrier layer by delamination. The inner part can be pulled off from the carrier layer.

A plurality of the analytical devices can be produced in a continuous process. The inner parts of the plurality of the analytical devices can be removed in a continuous process. The inner parts of the plurality of the analytical devices can be removed in a continuous web process, by continuously pulling off a waste web containing the inner parts.

The cover layer can comprise a plurality of parts and/or layers. The cover layer can comprise an analytical detection film. The analytical detection film can comprise at least one detector material. The detector material can be adapted to perform at least one detection reaction in the presence of an analyte to be detected. At least one detectable parameter of the detector material can change due to the detection reaction. The analytical detection film can comprise a layer setup. The layer setup can have at least one detection layer having the detector material. The layer setup can further have at least one additional layer. Specifically, at least one additional layer can be interposed in between the detection layer and the capillary element and/or at least one additional layer interposed in between the detection layer and the carrier layer. The additional layer can be at least one of a white pigment layer or a removal layer for removing particulate components of a sample.

The analytical device can be an analytical test element adapted for determining at least one parameter of a sample applied to the analytical device. The at least one parameter can be a concentration of at least one analyte contained in the sample.

The analytical device can be selected from the group comprising a test strip and a test tape.

At least one inspection tool can be used for detecting cutting lines generated by the cutting tools. At least one control device can be used for controlling at least one of the cutting tools in accordance with a result provided by the inspection tool.

At least one of the cutting tools, such as a first one of the cutting tools, can further generate at least one separation line in the spacer layer, for separating neighboring analytical devices in a continuous process, specifically at least one perforation line.

A production device for the production of at least one analytical device is disclosed. The production device can comprise at least one carrier layer supply device for providing at least one carrier layer; at least one spacer layer supply device for providing at least one spacer layer; at least one spacer layer application device for applying the spacer layer on top of the carrier layer; at least one cover layer supply device for providing at least one cover layer; at least one cover layer application device for applying the cover layer on top of the spacer layer; and at least two cutting tools. The production device can be adapted for cutting out at least one capillary channel of the capillary element from the spacer layer by using the cutting tools. The cutting tools can be complementing one another to form a contour of the capillary channel. The production device can be adapted to perform the production. An analytical device producible by the process can refer to a process for the production of at least one analytical device.

In FIGS. 1-6, various parts of a production device 110 for a continuous production of analytical devices 112 are shown. Analytical devices 112 which may be manufactured by using the production device 110 are shown in FIG. 7, which, for illustrative purposes, will be explained in the following.

Thus, a plurality of analytical devices 112 may be produced, which, in this embodiment, specifically may be designed as test strips 114 for detecting at least one analyte in a body fluid. The test strips 114 can be manufactured in a continuous process, as parts of a web 116, wherein the analytical devices 112 can be cut from the web 116 at separation lines 118.

The web 116 can contain a carrier layer 120, a spacer layer 122, and, in this embodiment, a plurality of cover layers 124, as will be outlined in further detail below. After a singulation step in which the analytical devices 112 can be cut from web 116, the carrier layer 120 can provide at least one carrier element 126 for each of the analytical devices 112. The spacer layer 122 can provide at least one spacer element 128 for each of the analytical devices 112. Similarly, the cover layer 124 can provide one or more cover elements 130 for each of the analytical devices 112.

Figure 7:
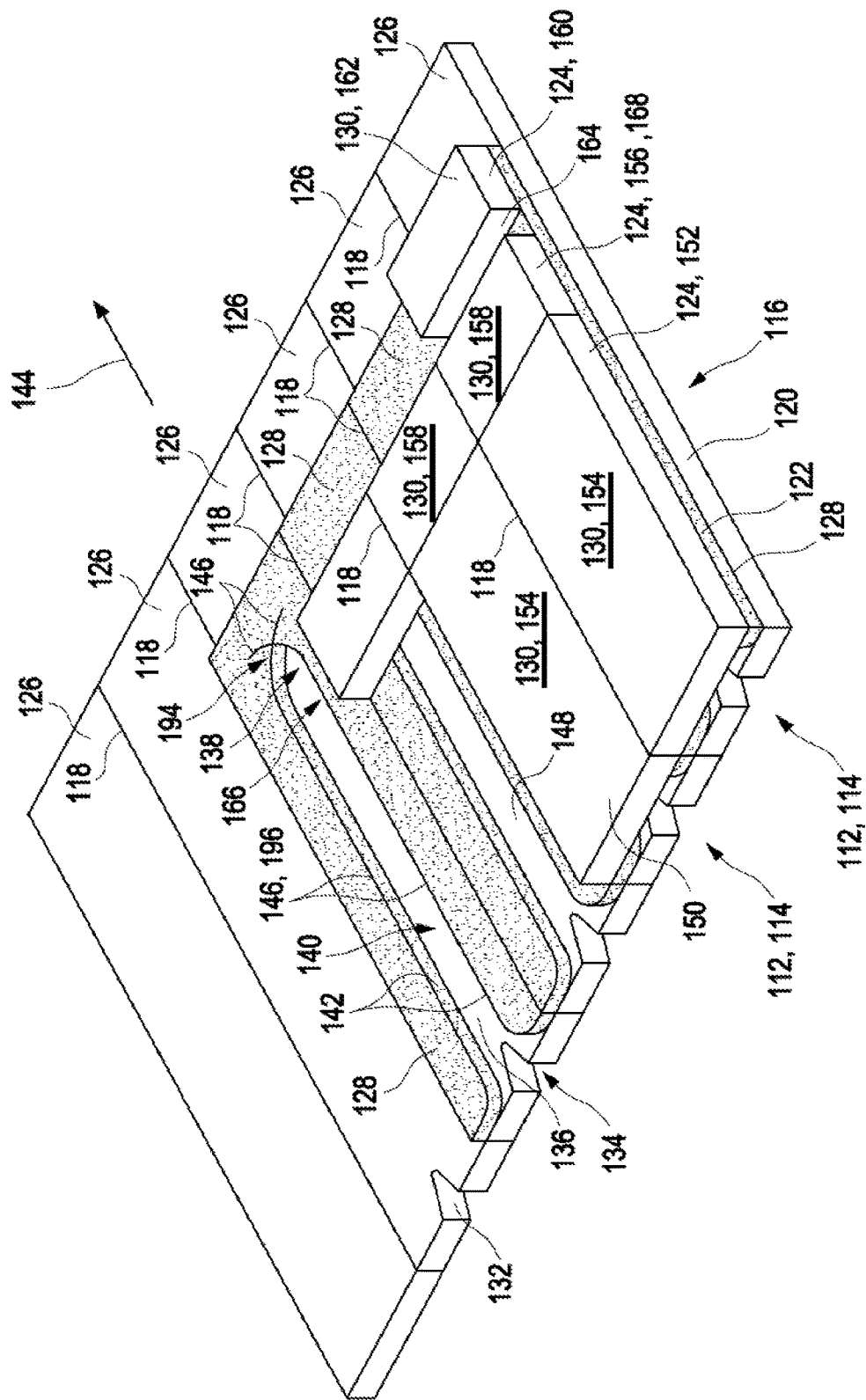
FIG. 7 illustrates partial perspective views of analytical devices producible by the process according to an embodiment of the present disclosure.

As can be seen in the partial perspective view of FIG. 7, the carrier elements 126 optionally may contain one or more notches 132 in an application region 134 of a capillary element 136 of the analytical devices 112. Each capillary element 136 may extend from the application region 134, such as in a straight fashion, to an end region 138 opposite the application region 134. Each capillary element 136, in this embodiment, can comprise a capillary channel 140. Besides, optionally, the capillary element 136 may contain one or more further capillary elements and/or more complex capillary structures, such as a structure having one or more further fluidic elements such as one or more reservoirs or other types of fluidic elements.

Each capillary channel 140, in this embodiment, can contain two opposing side walls 142 which, as an example, can be parallel side walls oriented substantially parallel to a longitudinal axis 144 of the analytical devices 112. The side walls 142, as will be explained in further detail below, can be formed by a cutting step in which at least two cutting lines 146 can be formed in the spacer layer 122. As an example, the cutting lines 146 can overlap at least in the end region 138, as can be seen in FIG. 7. Further, during manufacturing, the cutting lines 146 may overlap in the application region 134.

The spacer layer 122 may be embodied as a double-sided adhesive tape and may be bonded onto the carrier layer 120 by an adhesive process. The carrier layer 120 and/or the carrier elements 126 thereby can form a bottom wall 148 of the capillary channels 140. Similarly, the cover layer 124 and/or the cover elements 130 may be bonded to the spacer layer 122 by an adhesive process and, thereby, may form a top wall 150 of the capillary channels 140.

The cover layer 124, as outlined above, may comprise a plurality of cover layers 124, and the at least one cover element 130 may comprise a plurality of cover elements 130. Thus, as an example, the at least one cover layer may comprise at least one cover foil 152, and each cover element 130 may comprise at least one cover foil element 154. Further, the cover layer 124 may comprise at least one analytical detection film 156, wherein the portions of the analytical detection film 156 can form analytical detection area 158. Additionally, the cover layer 124 may comprise a protective foil 160, and each cover element 130 may comprise a protective element 162. In between the protective elements 162 and the analytical detection area 158, a gap 164 may remain, which may provide an air vent during filling of the capillary element 136. Thus, a sample, such as a fluid sample and specifically a sample of a body fluid, may be applied to the application region 134 and, by capillary forces, may be sucked into the capillary channel 140. In a detection region 166 underneath the analytical detection area 158, the sample may react with at least one detector material 168 contained within the analytical detection film 156.

As outlined above, the capillary channel 140 can be manufactured by at least one cutting step, providing at least two cutting lines 146 for the side walls 142 of the capillary channel 140. In FIG. 1, cutting tools 170 are shown, which may be part of an embodiment of a production device 110. The cutting tools can comprise a first cutting tool 172 and a second cutting tool 174, which can be offset from one another in a transport direction 176 of a spacer layer 122 which can be cut by these cutting tools 170. The cutting tools 170, in this embodiment, can be embodied as rotary cutting tools 178, each having a cutting cylinder 180 and a counter cylinder 182 interacting with the cutting cylinder 180. Each of the cutting cylinders 180 can have cutting edges 184 protruding from a circumferential surface 186 of the cutting cylinders 180. The spacer layer 122 can move through calender nips 188 between the cutting cylinders 180 and their respective counter cylinders 182, thereby being cut by the cutting edges 184, wherein cutting lines 146 can be generated. Thereof, the first cutting tool 172 can generate first cutting lines 190, whereas the second cutting tool 174 can generate second cutting lines 192. The first and second cutting lines 190, 192 can complement one another to form opposing side walls 142 of the capillary channel 140, as shown e.g. in FIG. 7.

As further can be seen in FIG. 1, as an example, the cutting lines 190, 192 may overlap in at least one overlapping region 194, in order to allow for a compensation of a varying distance $d_1$, $d_2$ between the first and second cutting lines 190, 192, as schematically depicted in FIG. 1. Thus, even though the distance $d_1$, $d_2$ may be varied at least to some extent, the first and second cutting lines 190, 192 can still complement one another to form a contour 196 of the capillary channels 140.

The first and second cutting tools 172, 174 may be individually controllable, as symbolically depicted by the −/+-symbol in FIG. 1. Thus, specifically, a phase shift and/or a frequency may be controlled. Thereby, the distances $d_1$, $d_2$ may be adjusted, by controlling the first and second cutting tools 172, 174. For the purpose of controlling the cutting tools 170, the production device 110 may comprise one or more control devices 198, adapted for controlling the cutting process of the cutting tools 170. The control device 198 may optionally be combined with at least one inspection tool 200. In FIG. 1, the inspection tool 200 symbolically is depicted by a camera. The at least one camera of the inspection tool 200 may be located downstream the first cutting tool 172 and/or downstream the second cutting tool 174. The inspection tool 200 may further comprise at least one image recognition device, such as a software for optically detecting the first cutting lines 190 and/or the second cutting lines 192, and the control device 198 may be designed to control the first cutting tool 172 and/or the second cutting tool 174 in order to adjust the positions of these first and/or second cutting lines 190, 192.

As can be seen in the exemplary embodiment of FIG. 1, the cutting edges 184 of the first and second cutting tools 172, 174 may have the shape of an elongated S. Alternatively, other shapes are possible, according to the desired contour 196 of the capillary channels 140. Thus, as an example, the cutting edges 184 may have, instead of a rounded shape, an angled shape, such as the shape of an angled S. Further, other shapes are possible.

Figure 2:
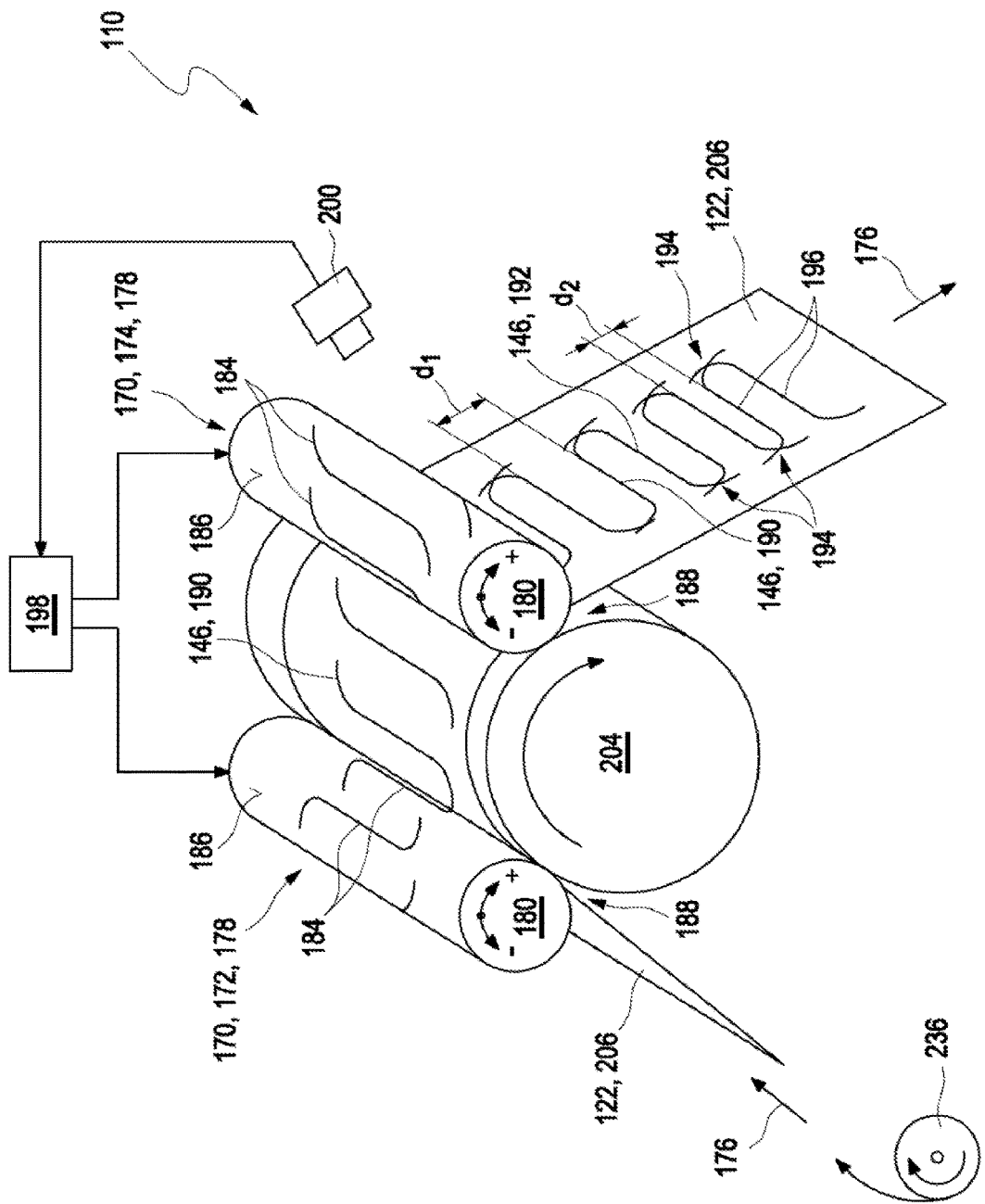
FIG. 2 illustrates an alternative embodiment of the setup of FIG. 1, with cutting cylinders and a common counter cylinder according to an embodiment of the present disclosure.

In FIG. 2, an alternative embodiment of the setup of FIG. 1 is shown. Again, cutting tools 170 can be used; having a first cutting tool 172 and a second cutting tool 174 located downstream the first cutting tool 172, with regard to a transport direction 176 of a spacer layer 122. As opposed to the embodiment in FIG. 1, however, in which the first and second cutting tools 172, 174 are embodied as cylinder pairs 202, each cylinder pair 202 having a cutting cylinder 180 and a counter cylinder 182, in the embodiment of FIG. 2, a common counter cylinder 204 can be used for the first and second cutting tools 172. Thus, the cutting cylinder 180 of the first cutting tool 172 and the common counter cylinder 204 can form a first cylinder pair, and the cutting cylinder 180 of the second cutting tool 174 and the common counter cylinder 204 can form a second cylinder pair, wherein calender nips 188 can be formed by these cylinders.

Again, optionally, at least one control device 198 may be provided, optionally in conjunction with at least one inspection tool 200. For further details, reference may be made to the embodiment of FIG. 1 above.

Figure 3:
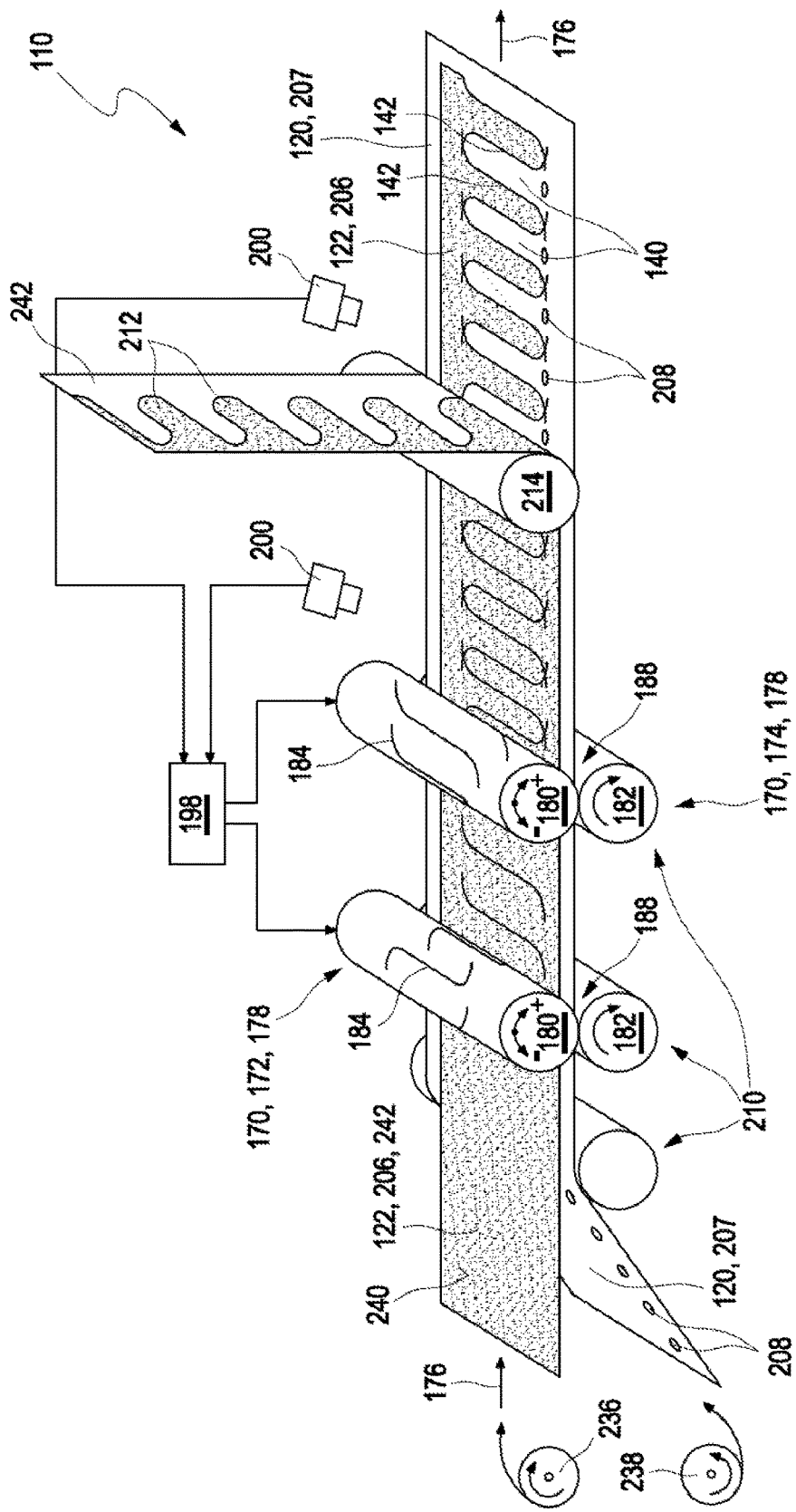
FIG. 3 illustrates a second alternative embodiment of the setup of FIG. 1, adapted for a kiss-cut-process in which a spacer layer is cut on top of a carrier layer according to an embodiment of the present disclosure.

In the embodiment shown in FIG. 1, the spacer layer 122 can be cut in a stand-alone-process, with the spacer layer 122 being supplied as a spacer layer tape 206. In FIG. 3, an alternative setup is shown, in which the cutting step can take place with the spacer layer tape 206 applied to a carrier layer 120, provided as a carrier layer tape 207. The carrier layer 120 and/or the carrier layer tape 207 may optionally contain a plurality of positioning marks 208, such as a plurality of perforations. By using at least one spacer layer application device 210, the carrier layer 120 and the spacer layer 122 may be applied to one another. Therein, as an example, first and second cutting tools 172, 174 as used in FIG. 1 may be used, which, by their calender nips 188, may be part of a lamination device of the spacer layer application device 210, for joining the spacer layer 122 and the carrier layer 120.

The cutting process, as described above with regard to FIG. 1, in the setup of FIG. 3 may take place with the spacer layer 122 applied on top of the carrier layer 120. Therein, the cutting step can be adjusted such that a cutting of the spacer layer 122 can take place, only, whereas the carrier layer 120 remains uncut. After the cutting step, inner parts 212 of the capillary channels 140 may be removed in a removal device 214, by pulling off these inner parts 212 in a continuous fashion. As can be seen, downstream the removal device 214, the capillary channels 140 can be formed. The removal device, in a similar fashion, may as well be combined with the setup of FIG. 2, alternatively.

As in FIGS. 1 and 2 above, optionally, a control device 198 may be provided. The at least one control device may be combined with at least one inspection tool 200. Thus, as an example, one inspection tool 200 may be located downstream the removal device 214, in order to inspect the position and/or the shape of the capillary channels 140. Thus, as an example, a relative position of the side walls 142 of the capillary channels 140 and the positioning marks 208 may be inspected, in order to control the cutting tools 172 and/or 174, accordingly. Thus, both side walls 142 may be controlled with respect to their relative position to the positioning markings 208. Further, a width of the capillary channels 140 and/or a divisor, i.e. a quotient of the width of the capillary channels and a distance between neighboring positioning marks 208 may be adjusted.

Figure 4:
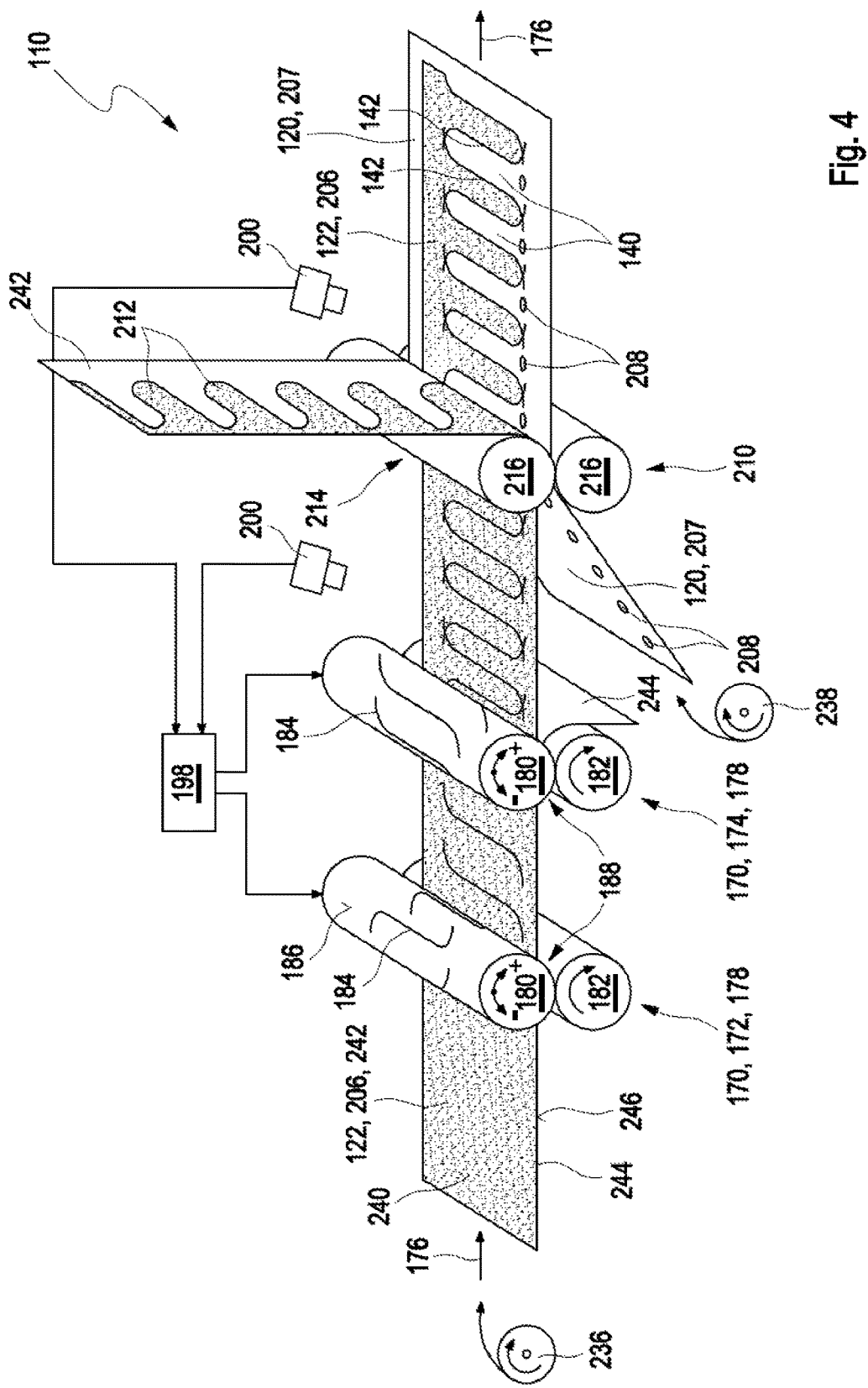
FIG. 4 illustrates an alternative setup in which the cutting step is performed without the carrier layer, and wherein the spacer layer is applied to the carrier layer after the cutting step according to an embodiment of the present disclosure.

The cutting step as disclosed in FIG. 3, with the cutting taking place with the spacer layer 122 applied to the carrier layer 120, can also be referred to as a kiss-cut-process. Alternatively, as shown in an alternative setup in FIG. 4, the application of the spacer layer 122 onto the carrier layer 120 may fully or partially take place after the cutting step. Thus, FIG. 4 shows a modification of the setup of FIG. 1 and/or of the setup of FIG. 3, wherein the spacer layer tape 206 can be applied to the carrier layer tape 207 after the cutting step performed by the cutting tools 170. Therein, again, a spacer layer application device 210 may be used, such as at least one calender, which may comprise cylinders 216. The spacer layer application device 210, in this embodiment or other embodiments, may as well be combined with the removal device 214 for removing the inner parts 212, such as by pulling off these inner parts 212 from the carrier layer 120, as in FIG. 3. For further optional details, such as details of the cutting step, details of the control of the cutting step or other details, reference may be made to the embodiments of FIGS. 1 through 3 disclosed above.

Figure 5:
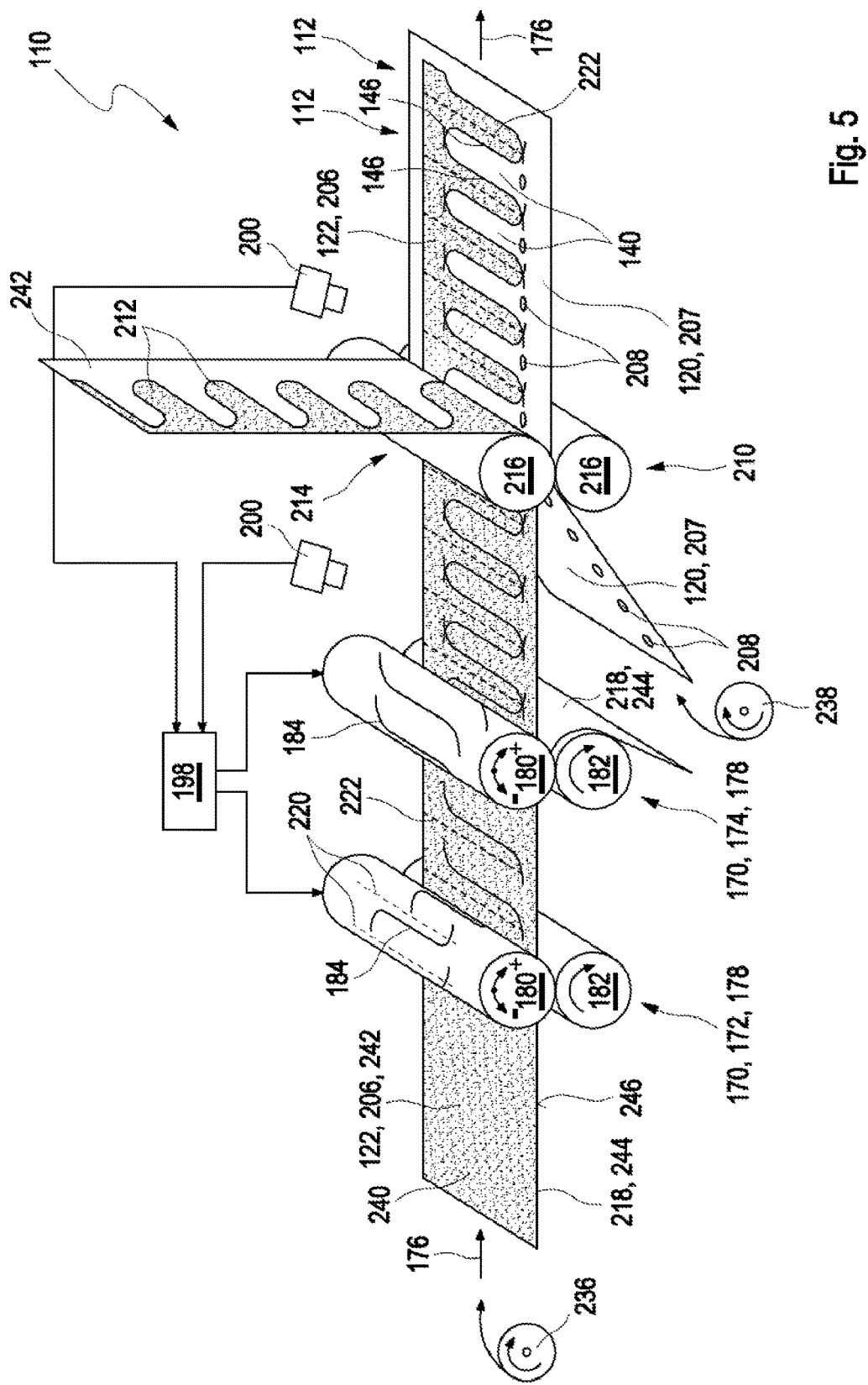
FIG. 5 illustrates a variation of FIG. 4, wherein the cutting step takes place with the spacer layer being applied to a support tape according to an embodiment of the present disclosure.

In FIG. 5, a further modification of the setup of FIG. 4 is shown. Again, as in the setup of FIG. 4, the spacer layer 122 can be applied to the carrier layer 120 after the cutting step. The cutting step, however, can take place with the spacer layer 206 applied to a support tape 218, wherein, after the cutting step, the support tape 218 can be pulled off from the spacer layer 122. For this purpose, an independent removal device may be used, or, as in FIG. 5, the counter cylinder 182 of the second cutting tool 174 may be used for pulling off the support tape 218. Subsequently, as in FIG. 4, the spacer layer 122 may be applied to the carrier layer 120.

Further, the embodiment of FIG. 5 shows that, in this embodiment or other embodiments, the cutting tools 170 may be adapted for providing more than the cutting lines 146 of the capillary channels 140. Thus, besides the cutting edges 184 for providing the cutting lines 146 for the capillary channels 140, one or both of the cutting tools 172, 174 may provide cutting edges 220 for generating separation lines 222 for separating neighboring analytical devices 112. As an example, the first cutting tool 172, located upstream the second cutting tool 174, can contain the cutting edges 220 for generating the separation lines 222. Thereby, the positioning of the cutting lines 146 generated by the second cutting tool 174 may be controlled with respect to the position of the separation lines 222, such as by using an inspection tool 200 located downstream the second cutting tools 174. Additionally or alternatively, as depicted in FIG. 5, an inspection tool 200 located downstream the removal device 214 may be used.

Figure 6A:
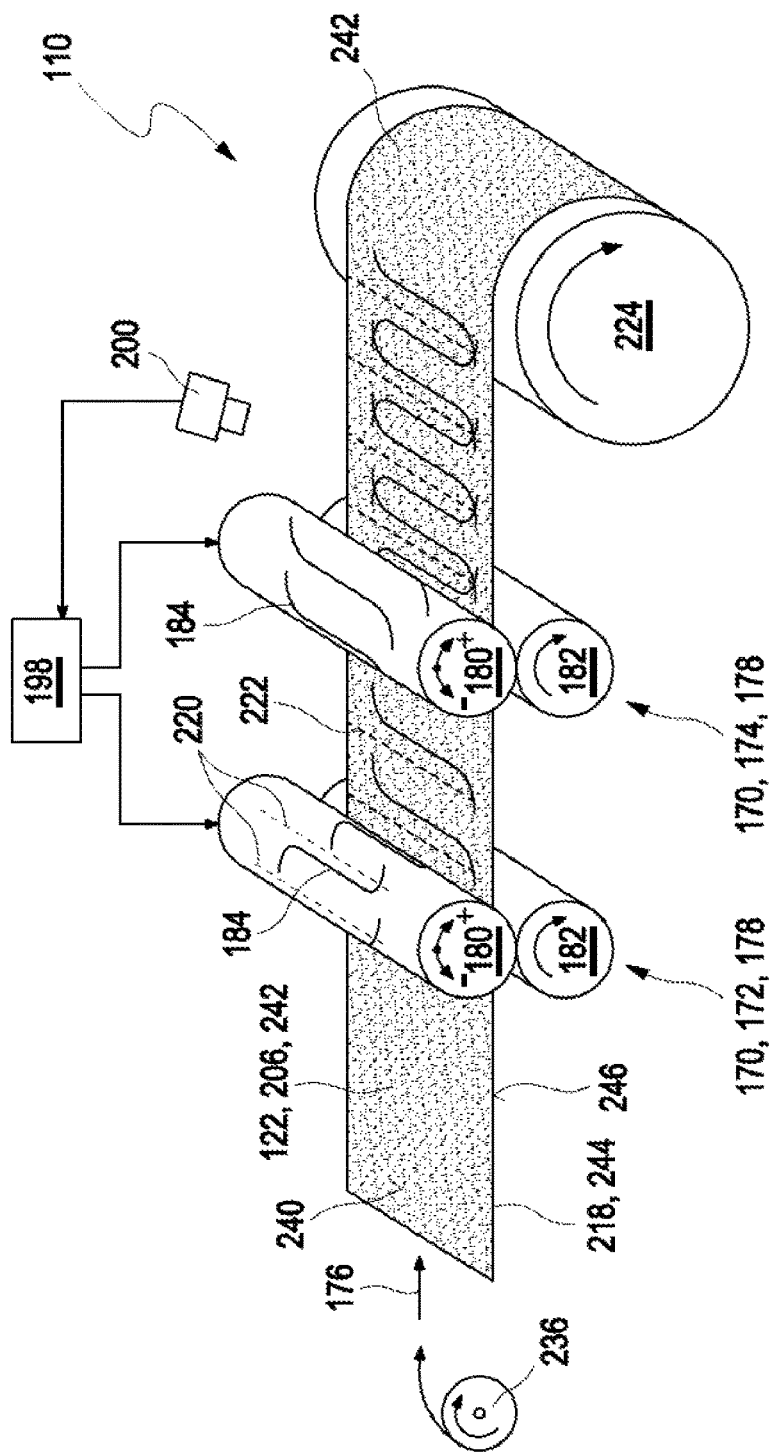
FIGS. 6A-C illustrate a production device, with the cutting device, the spacer layer application device and the cover layer application device, in various views according to an embodiment of the present disclosure.
Figure 6:
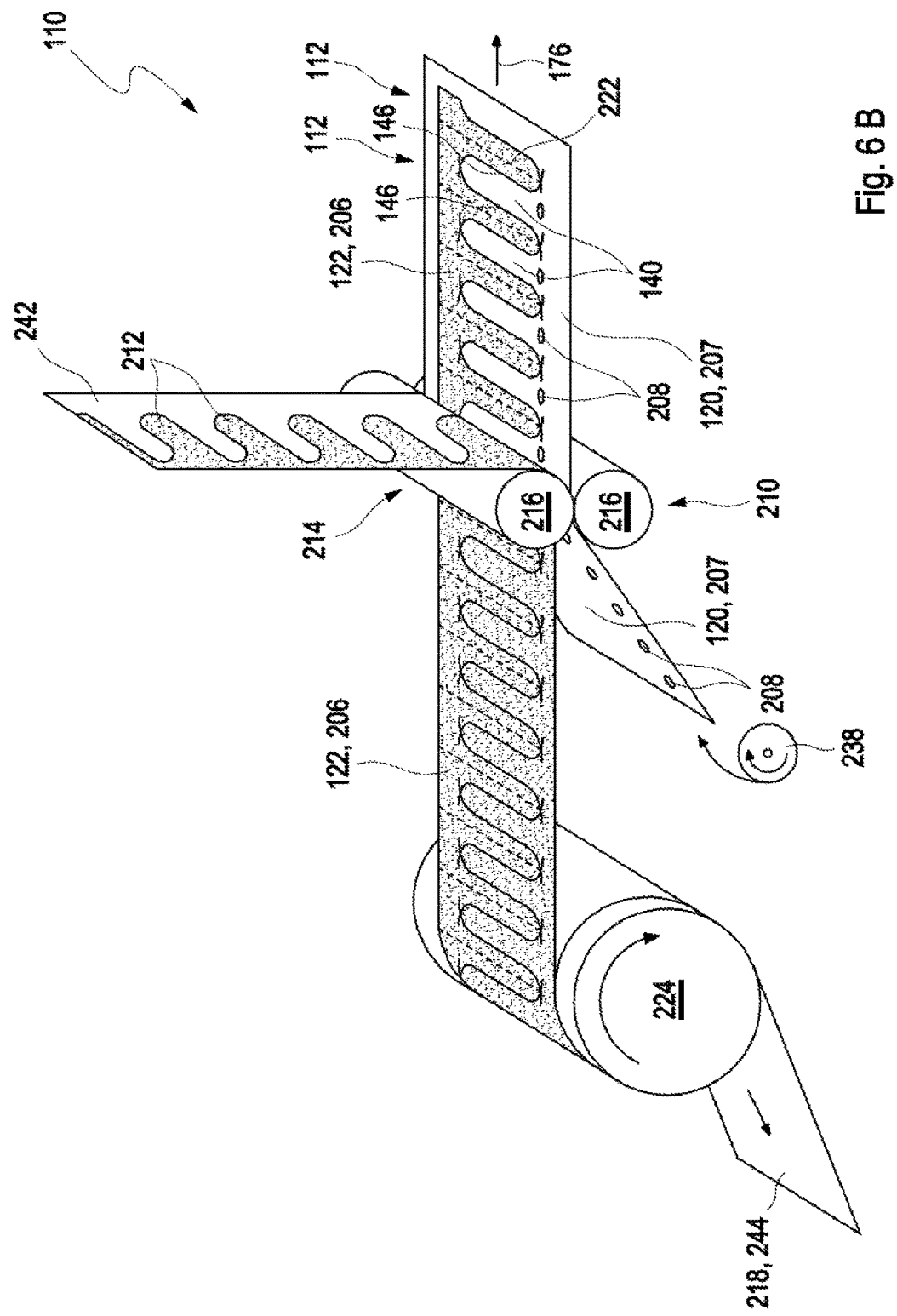
Figure 6:
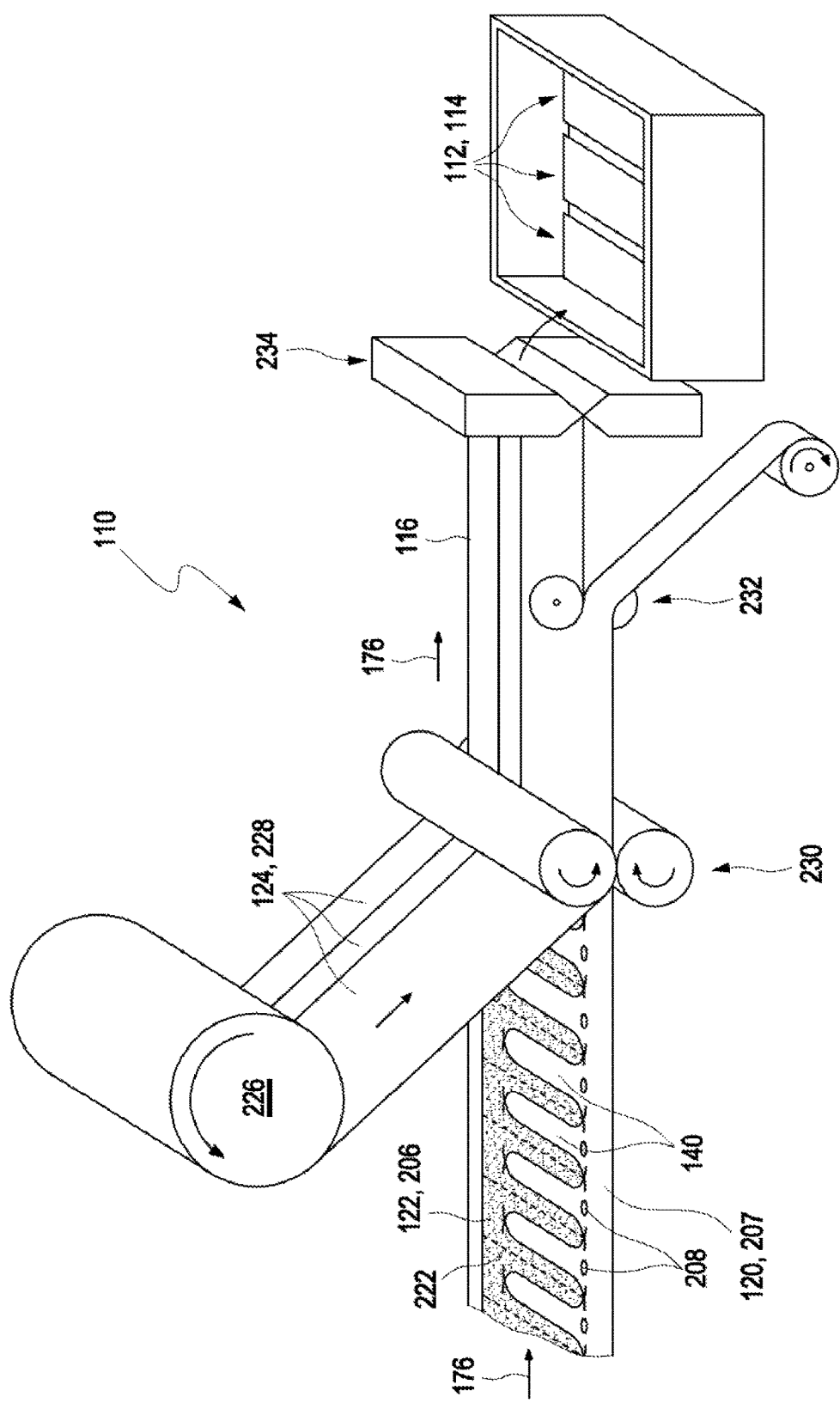

The production device 110 as depicted in the embodiments of FIGS. 1-5 may easily be separated into independent partial devices. This will be shown, by using a modification of the setup of FIG. 5, in FIGS. 6A-C. Thus, FIG. 6A shows a first part of production device 110, containing the cutting tools 170, for cutting the spacer layer 122. After the cutting step, which specifically may take place with the spacer layer 120 applied to a support tape 218, the intermediate product may be stored on a storage cylinder 224.

FIG. 6B shows a partial device of the production device 110, in which, starting with the storage cylinder 224 and the intermediate product obtained by using the setup of FIG. 6A, the support tape 218 can be pulled off from the intermediate product. Subsequently, as in FIG. 5, the cut spacer layer 122 can be applied to a carrier layer 120. Further, inner parts 212 may be pulled off in a removal device 214.

In FIG. 6C, a further part of the production device 110 is shown, which may be combined with the part shown in FIG. 6B, starting with the cut spacer layer 122 applied to the carrier layer 120 and the inner parts 212 removed, as obtained by the setup of FIG. 6B. Further, at least one cover layer supply device 226, such as one or more reels, may be used, for providing one or more cover layers 124, such as in the form of one or more cover layer tapes 228. In one or more cover layer application devices 230, such as one or more calenders, the cover layer 124 may be applied to the intermediate product, containing the carrier layer 120 and the cut spacer layer 122. Further, one or more cutting devices 232 may be used, for removing unwanted parts of the analytical devices 112, and one or more singulation devices 234 may be used, for cutting the individual analytical devices 112, such as the test strips 114, from the web 116. It shall be noted that other embodiments are feasible. Further, the embodiments shown in the FIGS. may be combined in any feasible fashion, as the skilled person will recognize.

Further, in FIG. 6C, the cover layer supply device 226 is shown, for supplying the cover layer 124. It shall be noted that, similar to the cover layer supply device 226, the spacer layer 122 and the carrier layer 120, specifically the spacer layer tape 206 and the carrier layer tape 207, may be provided in a similar fashion, by using a spacer layer supply device 236 and a carrier layer supply device 238, respectively. As an example, as for the cover layer supply device 226, these supply devices 236, 238 can be continuous supply devices, such as supply reels. Various embodiments, however, are feasible.

In the various embodiments of the production device 110 and of the method and process, the spacer layer tape 206 may fully or partially be covered by one or more liners. The one or more liners may be used for protecting the spacer layer tape 206 from impurities or mechanical influences and/or may be used for covering adhesive surfaces of the spacer layer tape 206. The one or more liners may even fully or partially be present during the cutting step and/or may be present in intermediate products. The one or more liners may be removed before connecting the respective surface of the spacer layer tape 206 to other elements. Various examples of using liners are shown in the embodiments.

Thus, as an example, an upper surface 240 of the spacer layer tape 206 in FIG. 3, as provided by spacer layer supply device 236, may be covered by a cover liner 242. The cutting step using cutting tools 170 may take place with the cover liner 242 still applied to the upper surface 240. By the removal device 214 and/or by a separate removal device, the cover liner 242, as depicted in FIG. 3, may fully or partially be removed from the upper surface 240. Alternatively, the portions of the spacer layer 122 on the right-hand side of removal device 214 may still remain covered by corresponding cutout portions of the cover liner 242. This choice may depend on further processing of the spacer layer 122. In case an immediate further processing takes place, the cover liner 242 may be removed, as depicted in FIG. 3, in order to provide a free upper surface of the spacer layer 122. In case the cutout spacer layer tape 206 on the right-hand side of removal device 214 is spooled onto a reel, as an intermediate product, it may be preferable to leave the cover liner 242 on top of the spacer layer tape 206. Other embodiments, however, are feasible.

Additionally or alternatively, one or more base liners 244 may be provided on a lower surface 246 of the spacer layer tape 206. The purpose of the one or more base liners 244 may basically be the same as for the at least one cover liner 242.

Thus, as an example, in FIG. 4, an embodiment is shown in which, by the spacer layer supply device 236, a spacer layer tape 206 having a cover liner 242 applied to its upper surface 240 and, additionally, having a base liner 244 applied to its lower surface 246 can be provided by the supply device 236. It shall be noted, however, that, in this embodiment or other embodiments, other options are feasible, such as providing a base liner 244 only or providing a cover liner 242 only.

In this embodiment, the cutting step being performed by the cutting tools 170 may be performed with liners 242 and 244 applied to the spacer layer tape 206. After the cutting step and before applying the carrier layer tape 207, the base liner 244 may be removed from the lower surface 246, in order to provide a free surface of the spacer layer tape 206. As shown in FIG. 4, the removal of the base liner 244 may take place in combination with the second cutting step, such as by using the counter cylinder 182 of the second cutting tool 174 as a removal device. Alternatively, an additional removal device may be used. The removed base liner 244 may be spooled onto a waste reel (not shown) or may be removed and disposed of in any other feasible way.

Similarly, as described above with reference to FIG. 3, the cover liner 242 may be removed, such as by using the spacer layer application device 210 and/or by using additional removal device. The removal may be a full removal of the cover liner 242 or a partial removal. In this regard, reference may be made to the options given above with reference to FIG. 3.

As outlined above, the function of the one or more liners 242, 244 may be a protective function and/or a mechanical function. Specifically, for adhesive surfaces, and interference of the adhesive surfaces such as a sticking of the adhesive surfaces to one or more of the cutting tools 170, may be prevented by using the one or more liners 242, 244. Additionally or alternatively, a mechanical function such as a mechanically protective function, may be provided. Further, a stabilization function may be provided by one or more of the liners 242, 244. Thus, the function of the one or more liners 242, 244 may fully or partially be combined with a support for carrier function. Consequently, as shown in the embodiment of FIG. 5 one or more of liners 242, 244, in this case the base liner 244, may fully or partially be combined with the at least one support tape 218. Thus, generally, one or both of the liners 242, 244 may provide a support carrier function and may be embodied as support tapes and/or support liners.

As outlined above, when providing an intermediate product comprising the spacer layer tape 206 in a cut fashion, as e.g. shown in FIG. 6A, the one or more optional liners 242, 244 may still be applied to one or both of surfaces 240, 246. Thus, when spooled onto storage cylinder 224, both liners 242, 244 may still be present.

Consequently, in FIG. 6B, in addition to the support tape 218 and/or the base liner 244, the cover liner 244 may be removed, such as after applying the spacer layer tape 206 to the carrier layer tape 207. Other ways of removal of liners 242, 244 are feasible.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A process for the production of at least one analytical device, the analytical device having at least one capillary element, the process comprising:
   providing at least one carrier layer;
   providing at least one spacer layer;
   applying the spacer layer on top of the carrier layer;
   providing at least one cover layer;
   applying the cover layer on top of the spacer layer; and
   cutting out at least one capillary channel of the capillary element from the spacer layer, wherein the cutting out is performed by using at least two cutting tools, wherein each cutting tool generates a cutting line that overlap and complementing one another to form a contour of the capillary channel and an overlapping region, wherein the overlapping region compensates for varying distances between the cutting lines, wherein the cutting tools are individually controlled with regard to at least one cutting parameter.

2. The process according to claim 1, wherein the cutting tools comprise at least one cutting cylinder having at least one cutting edge.

3. The process according to claim 2, wherein the cutting tools further comprise at least one counter cylinder interacting with the cutting cylinder.

4. The process according to claim 2, wherein the cutting cylinder comprises a plurality of cutting edges located on a circumferential surface of the cutting cylinder.

5. The process according to claim 4, wherein the cutting edges are S-shaped.

6. The process according to claim 2, wherein the cutting edges of the at least two cutting tools have a mirror symmetry.

7. The process according to claim 1, wherein the cutting out is at least partially performed before applying the spacer layer on top of the carrier layer, wherein, during the cutting out, the spacer layer is located on top of at least one support tape, wherein, after the cutting out, the support tape is removed and the spacer layer is applied on top of the carrier layer.

8. The process according to claim 1, wherein at least one cutting line is generated within the spacer layer.

9. The process according to claim 1, wherein the process further comprises, at least one singulation, wherein the analytical devices are cut from a web containing the carrier layer, the spacer layer and the cover layer.

10. The process according to claim 1, wherein the capillary channel comprises at least two side walls, wherein the side walls are produced during the cutting, wherein at least a first one of the side walls is produced by a first cutting tool, and wherein at least a second one of the side walls is produced by a second cutting tool.

11. The process according to claim 1, wherein the cutting is performed in a position-controlled fashion by using one or both of carrier layer positioning marks within the carrier layer and spacer layer positioning marks within the spacer layer.

12. The process according to claim 1, wherein, in the cutting, an inner part of the capillary channel is separated from a remainder of the spacer layer, wherein the inner part is removed from the carrier layer.

13. The process according to claim 1, wherein the cover layer comprises an analytical detection film.

* * * * *